US007850685B2

(12) United States Patent
Kunis et al.

(10) Patent No.: US 7,850,685 B2
(45) Date of Patent: Dec. 14, 2010

(54) ABLATION CATHETER

(75) Inventors: Christopher G. Kunis, San Diego, CA (US); Ricardo David Roman, San Diego, CA (US); Alexander J. Asconeguy, Murrieta, CA (US); J. Christopher Flaherty, Topsfield, MA (US); Randell L. Werneth, San Diego, CA (US)

(73) Assignee: Medtronic Ablation Frontiers LLC, Minneapolis, MN (US)

( * ) Notice: Subject to any disclaimer, the term of this patent is extended or adjusted under 35 U.S.C. 154(b) by 1058 days.

(21) Appl. No.: 11/471,467

(22) Filed: Jun. 20, 2006

(65) Prior Publication Data

US 2007/0083194 A1 Apr. 12, 2007

Related U.S. Application Data

(60) Provisional application No. 60/692,416, filed on Jun. 20, 2005.

(51) Int. Cl.
*A61B 18/14* (2006.01)
(52) U.S. Cl. ...................................................... 606/41
(58) Field of Classification Search ................... 606/41
See application file for complete search history.

(56) References Cited

U.S. PATENT DOCUMENTS

| | | | |
|---|---|---|---|
| 3,516,412 A | 6/1970 | Ackerman | |
| 3,951,136 A | 4/1976 | Wall | 128/2.06 E |
| 4,017,903 A | 4/1977 | Chu | |
| 4,112,952 A | 9/1978 | Thomas et al. | |
| 4,411,266 A | 10/1983 | Cosman | |
| 4,432,377 A | 2/1984 | Dickhudt | |
| 4,660,571 A | 4/1987 | Hess et al. | |
| 4,699,147 A | 10/1987 | Chilson et al. | |
| 4,785,815 A | 11/1988 | Cohen | |
| 4,860,769 A | 8/1989 | Fogarty | |
| 4,869,248 A | 9/1989 | Narula | |
| 4,882,777 A | 11/1989 | Narula | |
| 4,896,671 A | 1/1990 | Cunningham et al. | |
| 4,907,589 A | 3/1990 | Cosman | |
| 4,920,980 A | 5/1990 | Jackowski | |
| 4,940,064 A | 7/1990 | Desai | |

(Continued)

FOREIGN PATENT DOCUMENTS

AU     5200671AA     10/2005

(Continued)

OTHER PUBLICATIONS

Oral et al., "Catheter ablation for paroxysmal atrial fibrillation: segmental pulmonary vein ostial ablation versus left atrial ablation," Circulation, vol. 108, pp. 2355-2360, 2003.

(Continued)

*Primary Examiner*—Lee S Cohen
(74) *Attorney, Agent, or Firm*—Christopher & Weisberg, P.A.

(57) ABSTRACT

Devices, systems and methods are disclosed for the mapping of electrical signals and the ablation of tissue. Embodiments include an ablation catheter that has an array of ablation elements attached to a deployable carrier assembly. The carrier assembly can be transformed from a compact, linear configuration to a helical configuration, such as to map and ablate pulmonary vein ostia.

67 Claims, 17 Drawing Sheets

U.S. PATENT DOCUMENTS

| | | |
|---|---|---|
| 4,966,597 A | 10/1990 | Cosman |
| 5,010,894 A | 4/1991 | Edhag .................... 128/785 |
| 5,016,808 A | 5/1991 | Heil |
| 5,083,565 A | 1/1992 | Parins |
| 5,100,423 A | 3/1992 | Fearnot |
| 5,156,151 A | 10/1992 | Imran |
| 5,184,621 A | 2/1993 | Vogel et al. .................. 128/642 |
| 5,215,103 A | 6/1993 | Desai |
| 5,228,442 A | 7/1993 | Imran |
| 5,230,349 A | 7/1993 | Langberg |
| 5,231,987 A | 8/1993 | Robson |
| 5,231,995 A | 8/1993 | Desai |
| 5,234,004 A | 8/1993 | Hascoet et al. |
| 5,239,999 A | 8/1993 | Imran |
| 5,255,679 A | 10/1993 | Imran |
| 5,279,299 A | 1/1994 | Imran |
| 5,281,213 A | 1/1994 | Milder et al. |
| 5,281,218 A | 1/1994 | Imran |
| 5,309,910 A | 5/1994 | Edwards et al. |
| 5,313,943 A | 5/1994 | Houser et al. |
| 5,318,525 A | 6/1994 | West et al. |
| 5,324,284 A | 6/1994 | Imran |
| 5,327,889 A | 7/1994 | Imran |
| 5,330,466 A | 7/1994 | Imran |
| 5,334,193 A | 8/1994 | Nardella |
| 5,342,295 A | 8/1994 | Imran |
| 5,342,357 A | 8/1994 | Nardella |
| 5,345,936 A | 9/1994 | Pomeranz et al. |
| 5,348,554 A | 9/1994 | Imran et al. |
| D351,652 S | 10/1994 | Thompson et al. |
| 5,364,352 A | 11/1994 | Cimino et al. |
| 5,365,926 A | 11/1994 | Desai |
| 5,370,644 A | 12/1994 | Langberg .................... 606/33 |
| 5,383,917 A | 1/1995 | Desai et al. |
| 5,391,147 A | 2/1995 | Imran et al. |
| 5,397,304 A | 3/1995 | Truckai |
| 5,397,339 A | 3/1995 | Desai |
| 5,400,783 A | 3/1995 | Pomeranz et al. |
| 5,404,638 A | 4/1995 | Imran |
| 5,406,946 A | 4/1995 | Imran |
| 5,411,025 A | 5/1995 | Webster, Jr. |
| 5,423,808 A | 6/1995 | Edwards et al. |
| 5,423,811 A | 6/1995 | Imran et al. |
| 5,433,198 A | 7/1995 | Desai |
| 5,433,739 A | 7/1995 | Sluijter et al. |
| 5,445,148 A | 8/1995 | Jaraczewski et al. |
| 5,462,521 A | 10/1995 | Brucker et al. |
| 5,462,545 A | 10/1995 | Wang |
| 5,465,717 A | 11/1995 | Imran et al. |
| 5,471,982 A | 12/1995 | Edwards et al. |
| 5,487,757 A | 1/1996 | Truckai et al. |
| 5,492,119 A | 2/1996 | Abrams |
| 5,500,011 A | 3/1996 | Desai |
| 5,507,802 A | 4/1996 | Imran |
| 5,509,411 A | 4/1996 | Littmann et al. |
| 5,527,279 A | 6/1996 | Imran |
| 5,533,967 A | 7/1996 | Imran |
| 5,536,267 A | 7/1996 | Edwards et al. |
| 5,540,681 A | 7/1996 | Strul et al. |
| 5,545,161 A | 8/1996 | Imran |
| 5,545,193 A | 8/1996 | Fleischman et al. |
| 5,545,200 A | 8/1996 | West et al. |
| 5,558,073 A | 9/1996 | Pomeranz et al. |
| 5,573,533 A | 11/1996 | Strul |
| 5,575,766 A | 11/1996 | Swartz et al. |
| 5,575,810 A | 11/1996 | Swanson et al. |
| 5,578,007 A | 11/1996 | Imran |
| 5,582,609 A | 12/1996 | Swanson et al. |
| 5,584,830 A | 12/1996 | Ladd et al. |
| 5,588,432 A | 12/1996 | Crowley |
| 5,588,964 A | 12/1996 | Imran et al. |
| 5,595,183 A | 1/1997 | Swanson et al. |
| 5,596,995 A | 1/1997 | Sherman et al. |
| 5,598,848 A | 2/1997 | Swanson et al. |
| 5,601,088 A | 2/1997 | Swanson et al. |
| 5,606,974 A | 3/1997 | Castellano et al. |
| 5,607,462 A | 3/1997 | Imran |
| 5,620,481 A | 4/1997 | Desai et al. |
| 5,626,136 A | 5/1997 | Webster |
| 5,630,425 A | 5/1997 | Panescu et al. |
| 5,630,837 A | 5/1997 | Crowley |
| 5,637,090 A | 6/1997 | McGee et al. |
| D381,076 S | 7/1997 | Thornton et al. |
| 5,645,064 A | 7/1997 | Littmann et al. |
| 5,645,082 A | 7/1997 | Sung et al. |
| 5,656,029 A | 8/1997 | Imran et al. |
| 5,657,755 A | 8/1997 | Desai |
| 5,658,278 A | 8/1997 | Imran et al. |
| 5,662,606 A | 9/1997 | Cimino et al. |
| 5,666,970 A | 9/1997 | Smith |
| 5,673,695 A | 10/1997 | McGee et al. |
| 5,680,860 A | 10/1997 | Imran |
| 5,681,280 A | 10/1997 | Rusk et al. |
| 5,682,885 A | 11/1997 | Littmann et al. |
| 5,685,322 A | 11/1997 | Sung et al. |
| 5,687,723 A | 11/1997 | Avitall |
| 5,693,078 A | 12/1997 | Desai et al. |
| 5,697,927 A | 12/1997 | Imran et al. |
| 5,697,928 A | 12/1997 | Walcott et al. |
| 5,699,796 A | 12/1997 | Littmann et al. |
| 5,702,438 A | 12/1997 | Avitall |
| 5,704,791 A | 1/1998 | Gillio |
| 5,706,809 A | 1/1998 | Littmann et al. |
| 5,711,298 A | 1/1998 | Littmann et al. |
| 5,716,389 A | 2/1998 | Walinsky et al. |
| 5,722,401 A | 3/1998 | Pietroski et al. |
| 5,722,975 A | 3/1998 | Edwards et al. |
| 5,724,985 A | 3/1998 | Snell et al. |
| 5,733,323 A | 3/1998 | Buck et al. |
| 5,735,280 A | 4/1998 | Sherman et al. |
| 5,741,320 A | 4/1998 | Thornton et al. |
| 5,766,152 A | 6/1998 | Morley et al. |
| 5,769,791 A | 6/1998 | Benaron et al. |
| 5,769,847 A | 6/1998 | Panescu et al. |
| 5,772,590 A | 6/1998 | Webster, Jr. |
| 5,775,327 A | 7/1998 | Randolph et al. |
| 5,782,239 A | 7/1998 | Webster, Jr. |
| 5,782,760 A | 7/1998 | Schaer |
| 5,782,828 A | 7/1998 | Chen et al. |
| 5,782,899 A | 7/1998 | Imran .................... 607/122 |
| 5,792,140 A | 8/1998 | Tu et al. |
| 5,800,482 A | 9/1998 | Pomeranz et al. |
| 5,810,740 A | 9/1998 | Paisner |
| 5,820,568 A | 10/1998 | Willis |
| 5,827,272 A | 10/1998 | Breining et al. |
| 5,837,001 A | 11/1998 | Mackey |
| 5,849,028 A | 12/1998 | Chen |
| 5,857,464 A | 1/1999 | Desai |
| 5,857,997 A | 1/1999 | Cimino et al. |
| 5,860,920 A | 1/1999 | McGee et al. |
| 5,863,291 A | 1/1999 | Schaer |
| 5,871,523 A | 2/1999 | Fleischman et al. |
| 5,873,865 A | 2/1999 | Morzewski et al. |
| 5,876,399 A | 3/1999 | Chia et al. |
| 5,881,732 A | 3/1999 | Sung et al. |
| 5,882,333 A | 3/1999 | Schaer et al. |
| 5,885,278 A | 3/1999 | Fleischman |
| 5,891,027 A | 4/1999 | Tu et al. |
| 5,891,135 A | 4/1999 | Jackson et al. |
| 5,891,137 A | 4/1999 | Chia et al. |
| 5,891,138 A | 4/1999 | Tu et al. |
| 5,893,847 A | 4/1999 | Kordis |
| 5,893,884 A | 4/1999 | Tu |
| 5,893,885 A | 4/1999 | Webster, Jr. |

| | | | | | | |
|---|---|---|---|---|---|---|
| 5,895,355 A | 4/1999 | Schaer | | 6,216,043 B1 | 4/2001 | Swanson et al. |
| 5,895,417 A | 4/1999 | Pomeranz et al. | | 6,216,044 B1 | 4/2001 | Kordis |
| 5,897,554 A | 4/1999 | Chia et al. | | 6,217,573 B1 | 4/2001 | Webster |
| 5,904,680 A | 5/1999 | Kordis et al. .................. 606/41 | | 6,217,576 B1 | 4/2001 | Tu et al. |
| 5,906,605 A | 5/1999 | Coxum | | 6,226,542 B1 | 5/2001 | Reisfeld |
| 5,910,129 A | 6/1999 | Koblish et al. | | 6,231,570 B1 | 5/2001 | Tu et al. |
| 5,911,720 A | 6/1999 | Bourne et al. ................. 606/41 | | 6,238,390 B1 | 5/2001 | Tu et al. |
| 5,913,854 A | 6/1999 | Maguire et al. | | 6,241,666 B1 | 6/2001 | Pomeranz et al. |
| 5,916,214 A | 6/1999 | Cosio et al. | | 6,241,724 B1 | 6/2001 | Fleischman et al. |
| 5,928,191 A | 7/1999 | Houser et al. | | 6,241,725 B1 | 6/2001 | Cosman |
| 5,931,835 A | 8/1999 | Mackey | | 6,241,726 B1 | 6/2001 | Chia |
| 5,935,063 A | 8/1999 | Nguyen | | 6,241,727 B1 | 6/2001 | Tu et al. |
| 5,938,694 A | 8/1999 | Jaraczewski et al. | | 6,241,728 B1 | 6/2001 | Gaiser et al. |
| 5,941,845 A | 8/1999 | Tu et al. | | 6,241,754 B1 | 6/2001 | Swanson et al. |
| 5,951,471 A | 9/1999 | de la Rama et al. | | 6,245,067 B1 | 6/2001 | Tu et al. |
| 5,954,719 A | 9/1999 | Chen et al. | | 6,245,089 B1 | 6/2001 | Daniel et al. |
| 5,957,842 A | 9/1999 | Littmann et al. | | 6,251,107 B1 | 6/2001 | Schaer |
| 5,960,796 A | 10/1999 | Sung et al. | | 6,256,540 B1 | 7/2001 | Panescu et al. |
| 5,967,978 A | 10/1999 | Littmann et al. | | 6,264,664 B1 | 7/2001 | Avellanet |
| 5,968,040 A | 10/1999 | Swanson et al. ............... 606/41 | | 6,267,746 B1 | 7/2001 | Bumbalough |
| 5,971,980 A | 10/1999 | Sherman | | 6,290,697 B1 | 9/2001 | Tu et al. |
| 5,992,418 A | 11/1999 | de la Rama et al. | | 6,293,943 B1 | 9/2001 | Panescu et al. |
| 5,997,532 A | 12/1999 | McLaughlin et al. | | 6,302,880 B1 | 10/2001 | Schaer |
| 6,001,093 A | 12/1999 | Swanson et al. | | 6,309,385 B1 | 10/2001 | Simpson |
| 6,001,095 A | 12/1999 | de la Rama et al. | | 6,312,425 B1 | 11/2001 | Simpson et al. |
| 6,002,956 A | 12/1999 | Schaer | | 6,319,251 B1 | 11/2001 | Tu et al. ....................... 606/41 |
| 6,004,269 A | 12/1999 | Crowley et al. ............. 600/439 | | 6,325,797 B1 | 12/2001 | Stewart et al. |
| 6,014,581 A | 1/2000 | Whayne et al. | | 6,332,880 B1 | 12/2001 | Yang et al. |
| 6,021,340 A | 2/2000 | Randolph et al. | | 6,332,881 B1 | 12/2001 | Carner et al. |
| 6,023,638 A | 2/2000 | Swanson | | 6,346,104 B2 | 2/2002 | Daly et al. |
| 6,029,091 A | 2/2000 | de la Rama et al. | | 6,353,751 B1 | 3/2002 | Swanson |
| 6,032,674 A | 3/2000 | Eggers et al. ............... 128/898 | | 6,360,128 B2 | 3/2002 | Kordis et al. |
| 6,033,403 A | 3/2000 | Tu et al. | | 6,370,435 B2 | 4/2002 | Panescu et al. |
| 6,042,580 A | 3/2000 | Simpson | | 6,371,955 B1 | 4/2002 | Fuimaono et al. |
| 6,045,550 A | 4/2000 | Simpson et al. | | 6,379,352 B1 | 4/2002 | Reynolds et al. |
| 6,048,329 A | 4/2000 | Thompson et al. | | 6,389,311 B1 | 5/2002 | Whayne et al. |
| 6,049,737 A | 4/2000 | Simpson et al. | | 6,391,024 B1 | 5/2002 | Sun et al. |
| 6,050,994 A | 4/2000 | Sherman | | 6,425,894 B1 | 7/2002 | Brucker et al. |
| 6,052,612 A | 4/2000 | Desai | | 6,428,536 B2 | 8/2002 | Panescu et al. |
| 6,053,937 A | 4/2000 | Edwards et al. ............. 607/104 | | 6,428,537 B1 | 8/2002 | Swanson et al. |
| 6,056,744 A | 5/2000 | Edwards | | 6,440,129 B1 | 8/2002 | Simpson |
| 6,059,778 A | 5/2000 | Sherman | | 6,447,506 B1 | 9/2002 | Swanson et al. |
| 6,063,077 A | 5/2000 | Schaer | | 6,451,015 B1 | 9/2002 | Rittman, III et al. |
| 6,063,082 A | 5/2000 | DeVore et al. ................ 606/45 | | 6,454,758 B1 | 9/2002 | Thompson et al. |
| 6,064,902 A | 5/2000 | Haissaguerre et al. | | 6,456,864 B1 | 9/2002 | Swanson et al. |
| 6,068,629 A | 5/2000 | Haissaguerre et al. | | 6,460,545 B2 | 10/2002 | Kordis |
| 6,070,094 A | 5/2000 | Swanson et al. | | 6,471,693 B1 | 10/2002 | Carroll et al. |
| 6,071,274 A | 6/2000 | Thompson et al. | | 6,471,699 B1 | 10/2002 | Fleischman et al. |
| 6,071,279 A | 6/2000 | Whayne et al. | | 6,475,213 B1 | 11/2002 | Whayne et al. |
| 6,071,281 A | 6/2000 | Burnside et al. | | 6,475,214 B1 | 11/2002 | Moaddeb |
| 6,071,282 A | 6/2000 | Fleischman .................. 606/41 | | 6,477,396 B1 | 11/2002 | Mest et al. |
| 6,074,351 A | 6/2000 | Houser | | 6,478,793 B1 | 11/2002 | Cosman et al. |
| 6,086,581 A | 7/2000 | Reynolds et al. | | 6,485,487 B1 | 11/2002 | Sherman |
| 6,088,610 A | 7/2000 | Littmann et al. | | 6,487,441 B1 | 11/2002 | Swanson et al. |
| 6,096,036 A | 8/2000 | Bowe et al. | | 6,488,678 B2 | 12/2002 | Sherman |
| 6,099,524 A | 8/2000 | Lipson et al. | | 6,490,468 B2 | 12/2002 | Panescu et al. |
| 6,106,522 A | 8/2000 | Fleischman et al. | | 6,493,586 B1 | 12/2002 | Stahmann et al. |
| 6,107,699 A | 8/2000 | Swanson | | 6,500,167 B1 | 12/2002 | Webster, Jr. |
| 6,115,626 A | 9/2000 | Whayne et al. | | 6,500,172 B1 | 12/2002 | Panescu et al. |
| 6,119,041 A | 9/2000 | Pomeranz et al. | | 6,514,246 B1 | 2/2003 | Swanson et al. |
| 6,120,476 A | 9/2000 | Fung et al. | | 6,517,536 B2 | 2/2003 | Hoovea et al. |
| 6,129,724 A | 10/2000 | Fleischman et al. | | 6,522,905 B2 | 2/2003 | Desai |
| 6,141,576 A | 10/2000 | Littmann et al. | | 6,529,756 B1 | 3/2003 | Phan et al. |
| 6,146,379 A | 11/2000 | Fleischman et al. | | 6,540,744 B2 | 4/2003 | Hassett et al. |
| 6,146,381 A | 11/2000 | Bowe et al. | | 6,542,773 B2 | 4/2003 | Dupree et al. |
| 6,165,169 A | 12/2000 | Panescu et al. | | 6,544,262 B2 | 4/2003 | Fleischman |
| 6,167,291 A | 12/2000 | Barajas et al. | | 6,551,271 B2 | 4/2003 | Nguyen |
| 6,171,305 B1 | 1/2001 | Sherman | | 6,554,794 B1 | 4/2003 | Mueller et al. |
| 6,171,306 B1 | 1/2001 | Swanson et al. | | 6,558,378 B2 | 5/2003 | Sherman et al. |
| 6,179,833 B1 | 1/2001 | Taylor | | 6,565,511 B2 | 5/2003 | Panescu et al. |
| 6,200,314 B1 | 3/2001 | Sherman | | 6,569,114 B2 | 5/2003 | Ponzi et al. |
| 6,212,426 B1 | 4/2001 | Swanson | | 6,569,162 B2 | 5/2003 | He |
| 6,214,002 B1 | 4/2001 | Fleischman et al. | | 6,569,163 B2 | 5/2003 | Hata et al. |

| | | |
|---|---|---|
| 6,572,612 B2 | 6/2003 | Stewart et al. |
| 6,574,492 B1 | 6/2003 | Ben-Haim et al. |
| 6,575,997 B1 | 6/2003 | Palmer et al. |
| 6,583,796 B2 | 6/2003 | Jamar et al. |
| 6,597,955 B2 | 7/2003 | Panescu et al. |
| 6,602,242 B1 | 8/2003 | Fung et al. |
| 6,605,087 B2 | 8/2003 | Swartz et al. |
| 6,607,505 B1 | 8/2003 | Thompson et al. |
| 6,607,520 B2 | 8/2003 | Keane |
| 6,613,046 B1 * | 9/2003 | Jenkins et al. ................ 606/41 |
| 6,616,657 B2 | 9/2003 | Simpson et al. |
| 6,625,482 B1 | 9/2003 | Panescu et al. |
| 6,628,976 B1 | 9/2003 | Fuimaono et al. |
| 6,632,223 B1 | 10/2003 | Keane |
| 6,635,056 B2 | 10/2003 | Kadhiresan et al. |
| 6,638,223 B2 | 10/2003 | Lifshitz et al. |
| 6,638,275 B1 | 10/2003 | McGaffigan et al. |
| 6,640,120 B1 | 10/2003 | Swanson et al. |
| 6,652,513 B2 | 11/2003 | Panescu et al. |
| 6,652,517 B1 | 11/2003 | Hall et al. |
| 6,658,279 B2 | 12/2003 | Swanson et al. |
| 6,669,692 B1 | 12/2003 | Nelson et al. |
| 6,669,693 B2 | 12/2003 | Friedman |
| 6,671,533 B2 | 12/2003 | Chen et al. |
| 6,690,972 B2 | 2/2004 | Conley et al. |
| 6,701,180 B1 | 3/2004 | Desai |
| 6,702,811 B2 | 3/2004 | Stewart |
| 6,711,428 B2 | 3/2004 | Haissaguerre |
| 6,730,078 B2 | 5/2004 | Simpson et al. |
| 6,738,673 B2 | 5/2004 | Desai |
| 6,740,080 B2 | 5/2004 | Jain et al. ..................... 606/34 |
| 6,743,225 B2 | 6/2004 | Sanchez et al. |
| 6,746,446 B1 | 6/2004 | Hill, III et al. |
| 6,752,804 B2 | 6/2004 | Simpson et al. |
| 6,761,716 B2 | 7/2004 | Kadhiresan et al. |
| 6,805,131 B2 | 10/2004 | Kordis |
| 6,813,520 B2 | 11/2004 | Truckai et al. |
| 6,814,732 B2 | 11/2004 | Schaer |
| 6,830,576 B2 | 12/2004 | Fleischman et al. |
| 6,866,662 B2 | 3/2005 | Fuimaono |
| 6,893,438 B2 | 5/2005 | Hall et al. |
| 6,893,439 B2 | 5/2005 | Fleischman |
| 6,893,442 B2 | 5/2005 | Whayne |
| 6,916,306 B1 | 7/2005 | Jenkins et al. |
| 6,936,047 B2 | 8/2005 | Nasab et al. |
| 6,939,349 B2 | 9/2005 | Fleischman et al. |
| 6,952,615 B2 | 10/2005 | Satake ........................ 607/102 |
| 6,955,173 B2 | 10/2005 | Lesh |
| 6,960,206 B2 | 11/2005 | Keane |
| 6,961,602 B2 | 11/2005 | Fuimaono et al. |
| 6,964,660 B2 | 11/2005 | Maguire et al. |
| 6,966,908 B2 | 11/2005 | Maguire et al. |
| 6,972,016 B2 | 11/2005 | Hill et al. |
| 6,973,339 B2 | 12/2005 | Govari |
| 6,987,995 B2 | 1/2006 | Drysen |
| 7,001,336 B2 | 2/2006 | Mandrusov et al. |
| 7,025,766 B2 | 4/2006 | Whayne et al. |
| 7,029,470 B2 | 4/2006 | Francischelli et al. |
| 7,029,471 B2 | 4/2006 | Thompson et al. |
| 7,044,135 B2 | 5/2006 | Lesh |
| 7,047,068 B2 | 5/2006 | Haissaguerre |
| 7,048,734 B1 | 5/2006 | Fleischman et al. |
| 7,048,756 B2 | 5/2006 | Eggers et al. |
| 7,077,823 B2 | 7/2006 | McDaniel |
| 7,094,235 B2 | 8/2006 | Francischelli |
| 7,099,711 B2 | 8/2006 | Frimaono et al. |
| 7,099,712 B2 | 8/2006 | Fuimaono et al. |
| 7,113,831 B2 | 9/2006 | Hooven |
| 7,115,122 B1 | 10/2006 | Swanson et al. |
| 7,118,568 B2 | 10/2006 | Hassett et al. |
| 7,122,031 B2 | 10/2006 | Edwards et al. |
| 7,151,964 B2 | 12/2006 | Desai et al. |
| 7,155,270 B2 | 12/2006 | Solis et al. |
| 7,156,843 B2 | 1/2007 | Skarda |
| 7,163,537 B2 | 1/2007 | Lee et al. |
| 2001/0020166 A1 | 9/2001 | Daly et al. |
| 2001/0029366 A1 | 10/2001 | Swanson et al. |
| 2001/0039415 A1 | 11/2001 | Francischelli et al. |
| 2001/0044625 A1 | 11/2001 | Hata et al. |
| 2001/0051803 A1 | 12/2001 | Desai et al. |
| 2002/0065465 A1 | 5/2002 | Panescu et al. |
| 2002/0120263 A1 | 8/2002 | Brown et al. |
| 2002/0126036 A1 | 9/2002 | Flaherty et al. |
| 2002/0161422 A1 | 10/2002 | Swanson et al. |
| 2002/0165532 A1 | 11/2002 | Hill, III et al. |
| 2003/0018330 A1 | 1/2003 | Swanson et al. |
| 2003/0093069 A1 | 5/2003 | Panescu et al. |
| 2003/0125730 A1 | 7/2003 | Berube et al. |
| 2003/0181819 A1 | 9/2003 | Desai |
| 2003/0195407 A1 | 10/2003 | Fuimaono et al. |
| 2003/0195501 A1 | 10/2003 | Sherman et al. |
| 2003/0199746 A1 | 10/2003 | Fuimaono et al. |
| 2003/0204185 A1 | 10/2003 | Sherman et al. |
| 2003/0204186 A1 | 10/2003 | Geistert |
| 2003/0208199 A1 | 11/2003 | Keane ......................... 606/41 |
| 2004/0015164 A1 | 1/2004 | Fuimaono et al. |
| 2004/0082947 A1 | 4/2004 | Oral et al. |
| 2004/0116921 A1 | 6/2004 | Sherman et al. |
| 2004/0133154 A1 | 7/2004 | Flaherty et al. |
| 2004/0138545 A1 | 7/2004 | Chen et al. |
| 2004/0143256 A1 | 7/2004 | Bednarek |
| 2004/0152980 A1 | 8/2004 | Desai |
| 2004/0158141 A1 | 8/2004 | Scheib |
| 2004/0181139 A1 | 9/2004 | Falwell et al. |
| 2004/0181249 A1 | 9/2004 | Torrance et al. |
| 2004/0182384 A1 | 9/2004 | Alfery |
| 2004/0236324 A1 | 11/2004 | Muller et al. .................. 606/45 |
| 2004/0247164 A1 | 12/2004 | Furnish |
| 2005/0010095 A1 | 1/2005 | Stewart et al. ............... 600/374 |
| 2005/0015084 A1 | 1/2005 | Hill et al. |
| 2005/0033137 A1 | 2/2005 | Oral et al. |
| 2005/0065512 A1 | 3/2005 | Schaer |
| 2005/0096644 A1 | 5/2005 | Hall et al. |
| 2005/0101946 A1 | 5/2005 | Govari et al. .................. 606/33 |
| 2005/0119651 A1 | 6/2005 | Fuimaono et al. |
| 2005/0148892 A1 | 7/2005 | Desai |
| 2005/0177146 A1 | 8/2005 | Sherman |
| 2005/0187545 A1 | 8/2005 | Hooven et al. ................ 606/41 |
| 2005/0234444 A1 | 10/2005 | Hooven |
| 2005/0240176 A1 | 10/2005 | Oral et al. |
| 2005/0251132 A1 | 11/2005 | Oral et al. |
| 2005/0256521 A1 | 11/2005 | Kozel |
| 2006/0030844 A1 | 2/2006 | Knight et al. |
| 2006/0084966 A1 | 4/2006 | Maguire et al. |
| 2006/0089637 A1 | 4/2006 | Sherman |
| 2006/0095030 A1 | 5/2006 | Avitall |
| 2006/0106375 A1 | 5/2006 | Sherman |
| 2006/0111700 A1 | 5/2006 | Sherman |
| 2006/0111701 A1 | 5/2006 | Oral et al. |
| 2006/0111702 A1 | 5/2006 | Oral et al. |
| 2006/0111703 A1 | 5/2006 | Kunis et al. |
| 2006/0111708 A1 | 5/2006 | Vanney et al. |
| 2006/0122526 A1 | 6/2006 | Berenfeld et al. |
| 2006/0142753 A1 | 6/2006 | Francischelli et al. |
| 2006/0189975 A1 | 8/2006 | Whayne et al. |
| 2006/0195082 A1 | 8/2006 | Francischelli |
| 2006/0206109 A1 | 9/2006 | Swanson |
| 2006/0241366 A1 | 10/2006 | Falwell et al. |
| 2007/0083193 A1 | 4/2007 | Werneth et al. |
| 2007/0083195 A1 | 4/2007 | Werneth et al. |
| 2007/0106293 A1 | 5/2007 | Oral et al. |

FOREIGN PATENT DOCUMENTS

| | | |
|---|---|---|
| CA | 2327322AA | 11/1999 |
| CA | 2327518AA | 11/1999 |
| CA | 2328064AA | 11/1999 |
| CA | 2328070AA | 11/1999 |
| CA | 2371935AA | 12/2000 |
| CA | 2222617 C | 7/2002 |
| CA | 2437140AA | 6/2004 |
| CA | 2492283AA | 7/2005 |
| CA | 2194061 C | 4/2006 |
| CA | 2276755 C | 5/2006 |
| CA | 2251041 C | 6/2006 |
| DE | 10218427 | 11/2003 |
| EP | 428812 B1 | 3/1995 |
| EP | 779059 A | 6/1997 |
| EP | 598742 B1 | 8/1999 |
| EP | 1210021 B1 | 6/2002 |
| EP | 879016 B1 | 10/2003 |
| EP | 1360938 A1 | 11/2003 |
| EP | 1364677 A2 | 11/2003 |
| EP | 1554986 A1 | 7/2005 |
| EP | 823843 B1 | 10/2005 |
| EP | 1384445 B1 | 2/2006 |
| EP | 1169976 B1 | 4/2006 |
| EP | 1415680 B1 | 4/2006 |
| EP | 1011437 B1 | 5/2006 |
| EP | 1658818 A1 | 5/2006 |
| EP | 1125549 B1 | 6/2006 |
| EP | 1182980 B1 | 6/2006 |
| EP | 1207798 B1 | 6/2006 |
| EP | 1321166 B1 | 7/2006 |
| EP | 1343427 B1 | 7/2006 |
| EP | 1690564 A1 | 8/2006 |
| EP | 828451 B1 | 9/2006 |
| EP | 1070480 B1 | 9/2006 |
| EP | 1014874 B1 | 12/2006 |
| EP | 1383437 B1 | 12/2006 |
| EP | 1455667 B1 | 1/2007 |
| EP | 957794 B1 | 7/2007 |
| JP | 2004188179 A | 7/2004 |
| SU | 1512622 A1 | 10/1989 |
| SU | 1544396 A1 | 2/1990 |
| SU | 1690786 A1 | 11/1991 |
| WO | WO90/06079 A1 | 6/1990 |
| WO | WO93/08756 A1 | 5/1993 |
| WO | WO93/25273 A1 | 12/1993 |
| WO | WO94/12098 A1 | 6/1994 |
| WO | WO96/10961 A1 | 4/1996 |
| WO | WO96/32885 A1 | 10/1996 |
| WO | WO96/32897 A1 | 10/1996 |
| WO | WO96/34558 A1 | 11/1996 |
| WO | WO96/34559 A1 | 11/1996 |
| WO | WO96/34560 A1 | 11/1996 |
| WO | WO96/34567 A1 | 11/1996 |
| WO | WO96/34569 A1 | 11/1996 |
| WO | WO96/34570 A1 | 11/1996 |
| WO | WO96/34650 A1 | 11/1996 |
| WO | WO96/34652 A1 | 11/1996 |
| WO | WO96/34653 A1 | 11/1996 |
| WO | WO96/36860 A2 | 11/1996 |
| WO | WO96/39967 A1 | 12/1996 |
| WO | WO97/15919 A1 | 5/1997 |
| WO | WO97/17893 A1 | 5/1997 |
| WO | WO97/17904 A1 | 5/1997 |
| WO | WO97/25917 A1 | 7/1997 |
| WO | WO97/25919 A1 | 7/1997 |
| WO | WO97/32525 A1 | 9/1997 |
| WO | WO97/36541 A1 | 10/1997 |
| WO | WO97/40760 A1 | 11/1997 |
| WO | WO97/42996 A1 | 11/1997 |
| WO | WO98/18520 A2 | 5/1998 |
| WO | WO98/19611 A1 | 5/1998 |
| WO | WO98/26724 A1 | 6/1998 |
| WO | WO98/28039 A2 | 7/1998 |
| WO | WO98/38913 A1 | 9/1998 |
| WO | WO 99/02096 | 1/1999 |
| WO | WO99/56644 A1 | 11/1999 |
| WO | WO99/56647 A1 | 11/1999 |
| WO | WO99/56648 A1 | 11/1999 |
| WO | WO99/56649 A1 | 11/1999 |
| WO | 0067656 | 11/2000 |
| WO | WO00/78239 A2 | 12/2000 |
| WO | WO02/060523 A2 | 8/2002 |
| WO | WO03/041602 A2 | 5/2003 |
| WO | WO03/089997 A2 | 10/2003 |
| WO | WO2005/027765 A1 | 3/2005 |
| WO | WO2005/027766 A1 | 3/2005 |
| WO | WO 2005/065562 | 7/2005 |
| WO | WO 2005/065563 | 7/2005 |
| WO | WO2005/104972 A2 | 11/2005 |
| WO | WO2006/017517 A2 | 2/2006 |
| WO | WO 2006/044794 | 4/2006 |
| WO | WO2006/049970 A2 | 5/2006 |
| WO | WO 2006/052651 | 5/2006 |
| WO | WO2006/052905 A2 | 5/2006 |
| WO | WO2006/055654 A1 | 5/2006 |
| WO | WO2006/055658 A1 | 5/2006 |
| WO | WO2006/055733 A1 | 5/2006 |
| WO | WO2006/055741 A1 | 5/2006 |
| WO | WO2007/001981 A2 | 1/2007 |

OTHER PUBLICATIONS

Oral et al., "Segmental ostial ablation to isolate the pulmonary veins during atrial fibrillation: feasibility and mechanistic insights," Circulation, vol. 106, pp. 1256-1262, 2002.

Nademanee et al., "A new approach for catheter ablation of atrial fibrillation: mapping of the electrophysiologic substrate," JACC, vol. 43, No. 11, pp. 2044-2053, 2004.

Wittkampf et al., "Radiofrequency ablation with a cooled porous electrode catheter," (abstract) JACC, vol. 11, No. 2, pp. 17a, Feb. 1988.

Oral et al.; U.S. Appl. No. 11/932,378 entitled "Ablation catheters and methods for their use," filed Oct. 31, 2007.

Werneth et al.; U.S. Appl. No. 12/116,753 entitled "Ablation therapy system and method for treating continuous atrial fibrillation," filed May 7, 2008.

Sherman et al.; U.S. Appl. No. 12/117,596 entitled 'RF energy delivery system and method, filed May 8, 2008.

Oral et al.; U.S. Appl. No. 12/176,115 entitled "Atrial ablation catheter adapted for treatment of septal wall arrhythmogenic foci and method of use," filed Jul. 18, 2008.

Kunis et al.; U.S. Appl. No. 12/197,425 entitled "Atrial ablation catheter and method of use," filed Aug. 25, 2008.

Werneth et al.; U.S. Appl. No. 12/245,625 entitled "Ablation catheter," filed Oct. 3, 2008.

European Patent Application 06773536.5 (1895927), Communication pursuant to Rule 114(2) EPC, Third Party Observation, 5 pages.

* cited by examiner

PRE-ARRANGED ARM DURING ASSEMBLY

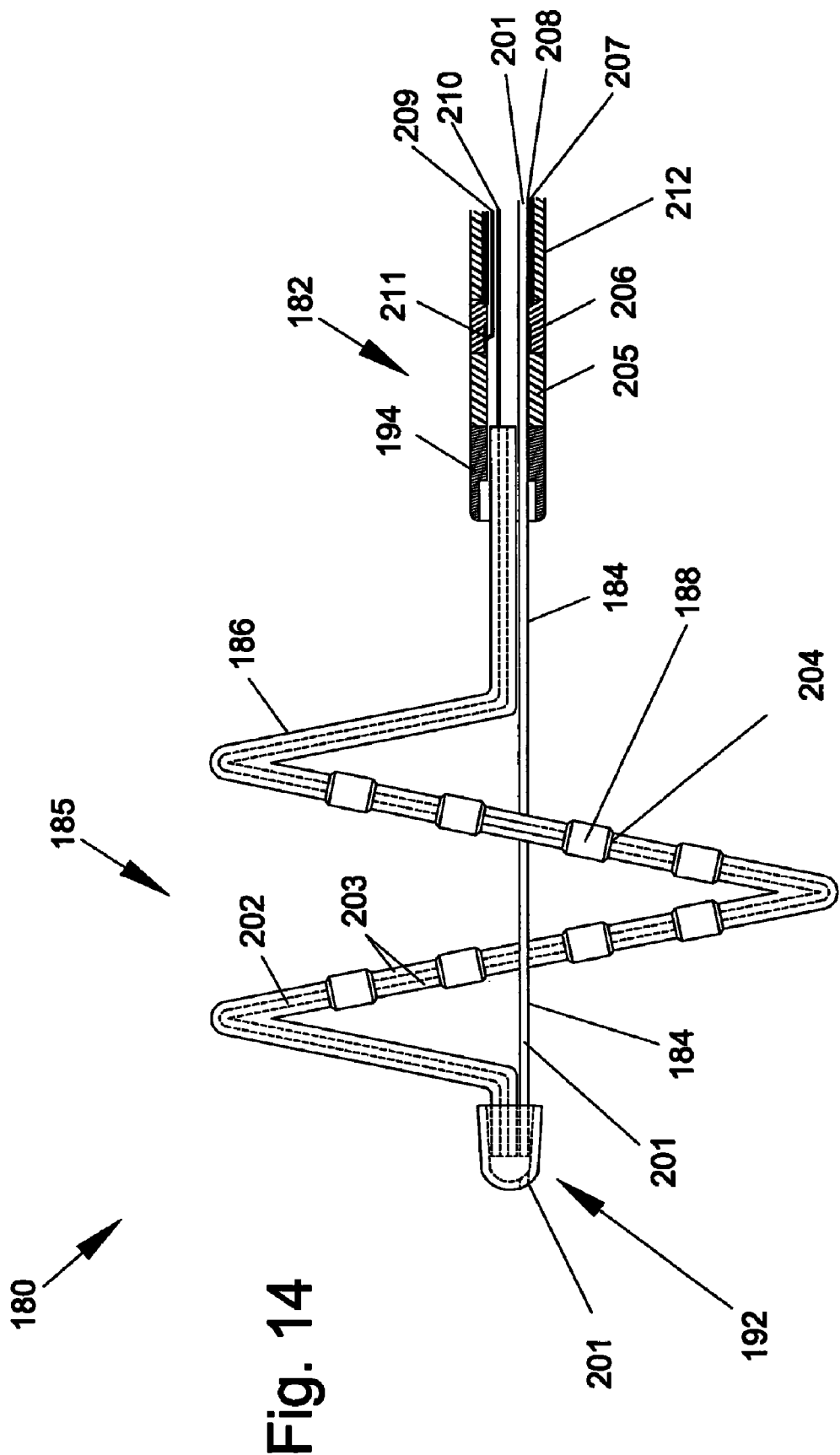

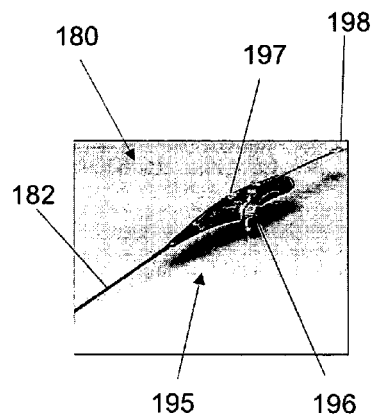 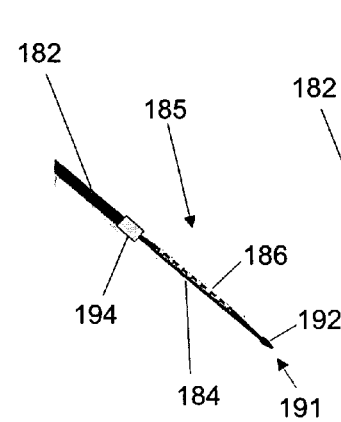 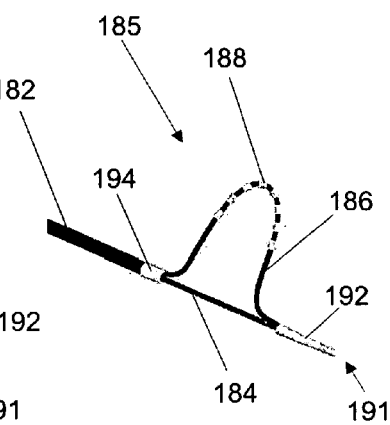
Fig. 15a    Fig. 15b    Fig. 15c
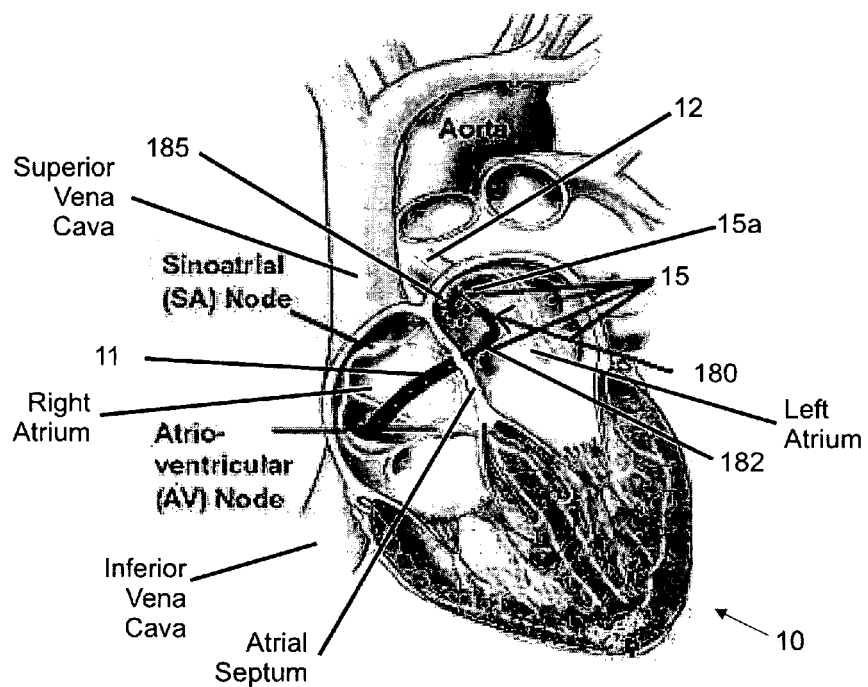
Fig. 15d

ABLATION CATHETER

STATEMENT OF RELATED APPLICATION

This application claims the benefit of U.S. Provisional Patent Application Ser. No. 60/692,416, filed Jun. 20, 2005, entitled "Pulmonary Vein Ablation Devices," which is incorporated by reference herein in its entirety.

FIELD OF THE INVENTION

The present invention relates generally to catheters and methods for performing targeted tissue ablation in a subject. In particular, the present invention provides devices comprising catheters having distal ends configured to pulmonary vein ostia, and methods for treating conditions (e.g., cardiac arrhythmias) with these and similar devices.

BACKGROUND OF THE INVENTION

Tissue ablation is used in numerous medical procedures to treat a patient. Ablation can be performed to remove undesired tissue such as cancer cells. Ablation procedures may also involve the modification of the tissue without removal, such as to stop electrical propagation through the tissue in patients with an arrhythmia. Often the ablation is performed by passing energy, such as electrical energy, through one or more electrodes causing the tissue in contact with the electrodes to heats up to an ablative temperature. Ablation procedures can be performed on patients with atrial fibrillation by ablating tissue in the heart.

Mammalian organ function typically occurs through the transmission of electrical impulses from one tissue to another. A disturbance of such electrical transmission may lead to organ malfunction. One particular area where electrical impulse transmission is critical for proper organ function is in the heart. Normal sinus rhythm of the heart begins with the sinus node generating an electrical impulse that is propagated uniformly across the right and left atria to the atrioventricular node. Atrial contraction leads to the pumping of blood into the ventricles in a manner synchronous with the pulse.

Atrial fibrillation refers to a type of cardiac arrhythmia where there is disorganized electrical conduction in the atria causing rapid uncoordinated contractions that result in ineffective pumping of blood into the ventricle and a lack of synchrony. During atrial fibrillation, the atrioventricular node receives electrical impulses from numerous locations throughout the atria instead of only from the sinus node. This overwhelms the atrioventricular node into producing an irregular and rapid heartbeat. As a result, blood pools in the atria that increases a risk for blood clot formation. The major risk factors for atrial fibrillation include age, coronary artery disease, rheumatic heart disease, hypertension, diabetes, and thyrotoxicosis. Atrial fibrillation affects 7% of the population over age 65.

Atrial fibrillation treatment options are limited. Lifestyle change only assists individuals with lifestyle related atrial fibrillation. Medication therapy assists only in the management of atrial fibrillation symptoms, may present side effects more dangerous than atrial fibrillation, and fail to cure atrial fibrillation. Electrical cardioversion often restores sinus rhythm, but has a high recurrence rate. In addition, if there is a blood clot in the atria, cardioversion may cause the clot to leave the heart and travel to the brain or to some other part of the body, which may lead to stroke. What are needed are new methods for treating atrial fibrillation and other conditions involving disorganized electrical conduction.

Various ablation techniques have been proposed to treat atrial fibrillation, including the Cox-Maze procedure, linear ablation of various regions of the atrium, and circumferential ablation of pulmonary vein ostia. The Cox-Maze procedure and linear ablation procedures are tedious and time-consuming, taking several hours to accomplish. Pulmonary vein ostial ablation is proving to be difficult to do, and has resulted in inadequate results and unacceptable trauma to the pulmonary veins. There is therefore a need for improved atrial ablation products and techniques.

SUMMARY OF THE INVENTION

According to a first aspect of the invention, an ablation catheter for an operator to treat a patient with an arrhythmia is disclosed. The catheter includes an elongate, flexible tubular body member have a proximal end, a distal end and a lumen therebetween. The catheter further includes a control shaft, coaxially disposed and slidingly received with the lumen of the tubular body member. A flexible carrier assembly is attached to the end of the control shaft and includes at least one ablation and/or mapping elements. Retraction of the control shaft causes the carrier assembly to transition from a compact, near linear configuration, to a helix or partial helix. In a preferred embodiment, the helix is less than 360°.

In a preferred embodiment, the carrier assembly can be withdrawn into a location within the tubular body member. In another preferred embodiment, the ablation catheter includes at least two carrier assemblies that can be transitioned between a compact, near linear configuration to a helix or partial helix. In yet another preferred embodiment, the catheter can be placed over a guidewire or includes an integral guidewire tip.

According to another aspect of the invention, an ablation catheter for an operator to treat a patient with an arrhythmia is disclosed. The catheter includes an elongate, flexible tubular body member have a proximal end, a distal end and a lumen therebetween. The catheter further includes a control shaft, coaxially disposed and slidingly received with the lumen of the tubular body member. A flexible carrier assembly is attached to the end of the control shaft and includes at least one ablation and/or mapping elements in an umbrella tip configuration. Retraction of the control shaft causes the carrier assembly to change shape, such as to conform to tissue surrounding one or more pulmonary veins entering the left atrium of a patient.

In a preferred embodiment, the ablation catheter includes a second carrier assembly, also in an umbrella tip configuration. In another preferred embodiment, the catheter includes an anchoring element, such as a balloon or expandable cage, for stabilizing and/or anchoring the ablation catheter in a pulmonary vein. In yet another preferred embodiment, the catheter includes an ultrasound element for directing ultrasound energy in a circular pattern toward tissue. In yet another preferred embodiment, one or more carrier arms of the umbrella tip can be rotated, stabilized, or otherwise manipulated to better conform to or stabilize with tissue such as pulmonary vein ostial tissue. In yet another preferred embodiment, the catheter can be placed over a guidewire or includes an integral guidewire tip. In yet another preferred embodiment, the catheter includes an advancable spline which can be used to position or stabilize the carrier assembly.

According to yet another aspect of the invention, an ablation catheter for an operator to treat a patient with an arrhythmia is disclosed. The catheter includes an elongate, flexible tubular body member have a proximal end, a distal end and a lumen therebetween. The catheter further includes a flexible carrier assembly comprising an inflatable balloon with mounted or embedded ablation and/or mapping elements.

BRIEF DESCRIPTION OF THE DRAWINGS

The accompanying drawings, which are incorporated in and constitute a part of this specification, illustrate various embodiments of the present invention, and, together with the description, serve to explain the principles of the invention. In the drawings:

FIG. 8b is an end view of the ablation catheter of FIG. 8a.

FIG. 8c is an end view of the collar of the ablation catheter of FIG. 8a.

FIG. 14 illustrates a side sectional view of a distal portion of an ablation catheter consistent with the present invention, in which the carrier assembly comprises a single carrier arm.

FIG. 15a illustrates a perspective view of a proximal portion of an ablation catheter consistent with the present invention, including a handle with multiple controls.

FIG. 15b illustrates a perspective view of a distal portion of the ablation catheter of FIG. 15a, in which the carrier assembly comprises a single carrier arm and the carrier assembly is in a fully compacted state.

FIG. 15c illustrates a perspective view of a distal portion of the ablation catheter of FIG. 15a, in which the carrier assembly comprises a single carrier arm and the carrier assembly is in the fully deployed state.

FIG. 15d illustrates the ablation catheter of FIGS. 15a through 15c after having been placed through a transeptal sheath and the carrier assembly deployed and contacting the ostium of the left superior pulmonary vein.

FIG. 17c illustrates an end view of the device of FIG. 17a.

DETAILED DESCRIPTION OF THE PREFERRED EMBODIMENTS

Figure 1:
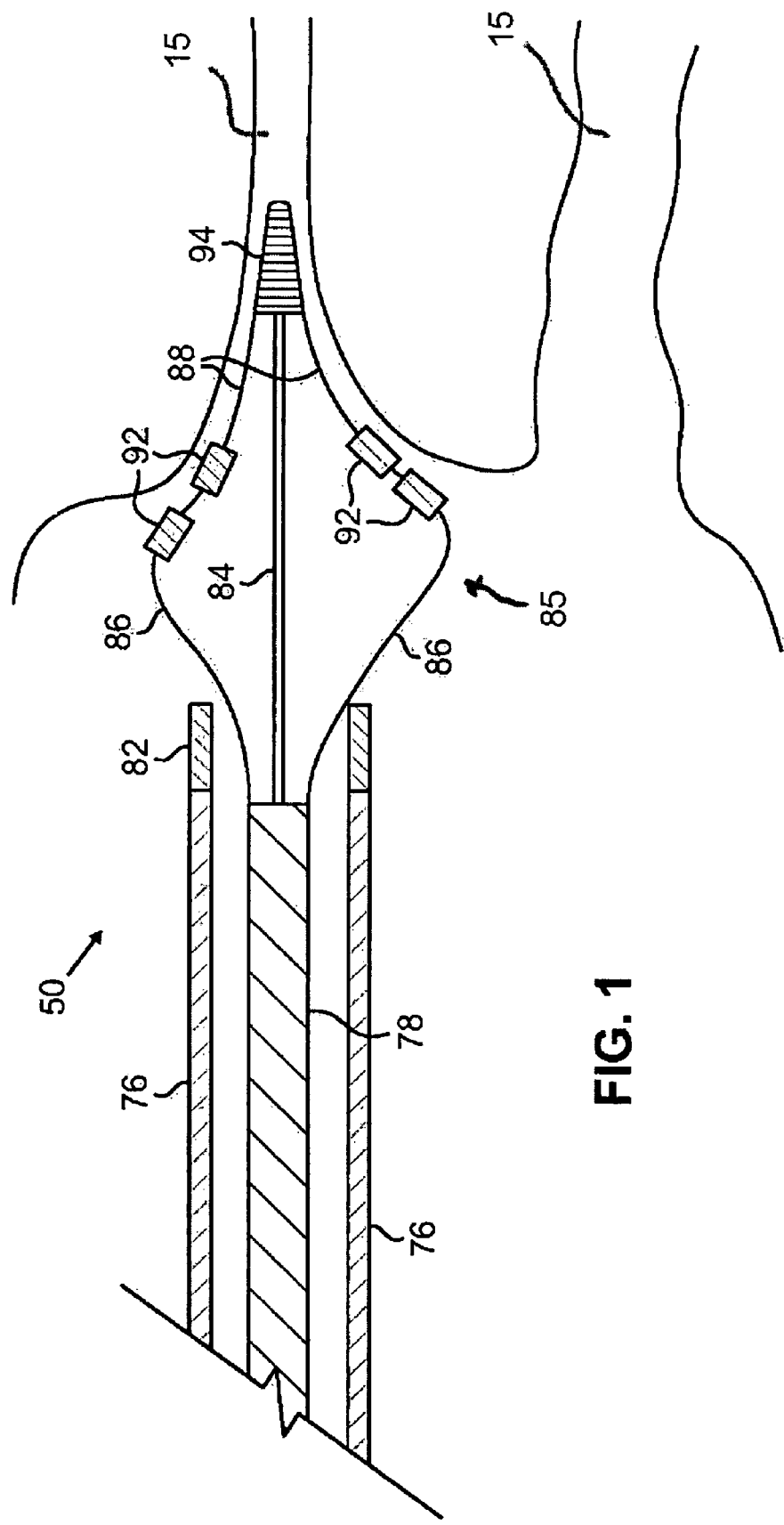
FIG. 1 illustrates a side sectional view of an ablation catheter, consistent with present invention, with the distal end inserted into a pulmonary vein of a patient.

Reference will now be made in detail to the present embodiments of the invention, examples of which are illustrated in the accompanying drawings. Wherever possible, the same reference numbers will be used throughout the drawings to refer to the same or like parts.

The present invention provides catheters for performing targeted tissue ablation in a subject. In preferred embodiments, the catheters comprise a tubular body member having a proximal end and distal end and preferably a lumen extending therebetween. The catheter is preferably of the type used for performing intracardiac procedures, typically being percutaneously introduced and advanced from the femoral vein in a patient's leg. Alternative methods involve percutaneous introduction into the jugular vein of the patient's neck, or other anatomical entry point that can be used to access the target location within the patient. The catheter is preferably introducable through a sheath and also preferably is advancable over a guidewire. The catheter preferably has a steerable tip that allows precise positioning of the distal portion such as when the distal end of the catheter needs to access a pulmonary vein of the left atrium of the patient's heart. The catheters include ablation elements mounted on one or more carrier arms of a flexible carrier assembly. Typical metals chosen for carrier assembly construction include but are not limited to: stainless steel, Nitinol, Elgiloy™, other alloys and combinations thereof. These ablation elements can be used to ablate and/or map electrical activity of tissue. The carrier assembly is attached to a control shaft that is coaxially disposed and slidingly received within the lumen of the tubular body member. The shape of the carrier assembly is adjusted by advancing or retracting the control shaft, such as to engage one or more ablation elements against cardiac tissue, typically pulmonary vein ostial tissue.

Arrays of ablation elements, preferably geometrically-adjustable electrode arrays, may be configured in a wide variety of ways and patterns. In particular, the present invention provides devices with multi-dimensional electrode arrays that provide electrical energy, such as radiofrequency (RF) energy, in monopolar (unipolar), bipolar or combined monopolar-bipolar fashion, as well as methods for treating conditions (e.g., atrial fibrillation, supra ventricular tachycardia, atrial tachycardia, ventricular tachycardia, ventricular fibrillation, and the like) with these devices. Alternative to or in combination with ablation elements that deliver electrical energy to tissue, other forms and types of energy can be delivered including but not limited to: sound energy such as acoustic energy and ultrasound energy; electromagnetic energy such as electrical, magnetic, microwave and radiofrequency energies; thermal energy such as heat and cryogenic energies; chemical energy such as energy generated by delivery of a drug; light energy such as infrared and visible light energies; mechanical and physical energy; radiation; and combinations thereof.

As described above, the normal functioning of the heart relies on proper electrical impulse generation and transmission. In certain heart diseases (e.g., atrial fibrillation) proper electrical generation and transmission are disrupted or are otherwise abnormal. In order to diagnose and/or prevent improper impulse generation and transmission from causing an undesired condition, the ablation catheters of the present invention may be employed.

One current method of treating cardiac arrhythmias is with catheter ablation therapy. Physicians make use of catheters to gain access into interior regions of the body. Catheters with attached electrode arrays or other ablating devices are used to create lesions that disrupt electrical pathways in cardiac tissue. In the treatment of cardiac arrhythmias, a specific area of cardiac tissue having aberrant conductive pathways, such as atrial rotors, emitting or conducting erratic electrical impulses, is initially localized. A user (e.g., a physician) directs a catheter through a main vein or artery into the interior region of the heart that is to be treated. The ablating element or elements are next placed near the targeted cardiac tissue that is to be ablated, such as a pulmonary vein ostium. After performing an electrical mapping procedure, the physician directs energy, provided by a source external to the patient, from one or more ablation elements to ablate the neighboring tissue and form a lesion. In general, the goal of catheter ablation therapy is to disrupt the electrical pathways in cardiac tissue to stop the emission of and/or prevent the propagation of erratic electric impulses, thereby curing the heart of the disorder. For treatment of atrial fibrillation, currently available methods and devices have shown only limited success and/or employ devices that are extremely difficult to use or otherwise impractical.

The ablation catheters of the present invention allow the generation of lesions of appropriate size and shape to treat conditions involving disorganized electrical conduction (e.g., atrial fibrillation). The created lesions are segmented and localized. The lesions may be linear or curvilinear, circumferential and partial circumferential, and/or continuous or discontinuous. The ablation catheters of the present invention are also practical in terms of ease-of-use and limiting risk to the patient, as well as significantly reducing procedure times. The lesions created by the ablation catheters are suitable for inhibiting the propagation of inappropriate electrical impulses in the heart for prevention of reentrant arrhythmias.

The catheters of the present invention can perform tissue ablation and/or mapping of electrical signals present in tissue. Patients, such as those with atrial fibrillation, are diagnosed and treated with the herein described mapping and/or ablation procedures. The catheters of the present invention are specifically applicable to mapping and ablation of the pulmonary vein ostia located in the left atrium of the patient's heart. These vein ostia are approximately 1.5 cm in diameter and often are non-circular in geometry, especially when a venous bifurcation is present proximate the ostia. The carrier assembly of the present invention may include one or more carrier arms that are configured to conform to these circular and non-circular contours of pulmonary vein ostia. One or more carrier arms, or groups of carrier arms, may be configured to be independently advancable and retractable, such as to properly engage pulmonary vein ostium tissue. The carrier arms are preferably made of Nitinol, and may have round, oval, triangular, rectangular, or trapezoidal cross-sectional geometry. The carrier arms may include compound splines or angles, such as to conform to pulmonary vein ostia and surrounding tissue. Each carrier arm may include one or more sensors, such as temperature sensors integral to an ablation element or mounted between two ablation elements, such as to measure tissue temperature and/or blood temperature. In a preferred embodiment, a temperature sensor is mounted to a carrier arm in a location more distal than the most distal ablation element, when the carrier assembly is in a deployed, ready to deliver ablation energy, configuration. Information recorded by the temperature sensor can be used by an energy delivery unit of the present invention as a threshold to avoid overheating of blood or tissue, as well as regulate power to a target temperature. A first carrier arm may have a different property than a second carrier arm, such as a different rigidity, a different number of ablation elements, or a different configuration of sensors such as temperature sensors.

The catheters of the present invention may be configured to be advanced into the heart of a patient over a previously placed guidewire, such as a standard interventional 0.035" guidewire. The catheter may include an inner lumen for the majority of its length, through which the guidewire is inserted, or the catheter may include a relatively short sidecar near its distal end, where the guidewire inserted through a lumen of the sidecar. The placement over the guidewire allows simplified positioning and re-positioning by an operator. The guidewire placement also provides stability such as to simplify maintaining the position of the catheter during energy delivery, typically 60 seconds.

The catheters of the present invention are configured to be inserted through the lumen of a previously placed transeptal sheath, such as a 9.5 French (Fr) steerable transeptal sheath. The catheter of the present invention preferably include an integral steering mechanism, such as one or more pull wires fixedly attached near a distal portion of the catheter and operably attached to a lever, knob or other control integral to a handle of the catheter. The steering can be used to deflect the carrier assembly and distal end of the catheter into the left and right pulmonary veins of the left atrium. The integral catheter steering can be used in conjunction a steerable transeptal sheath. Multiple pull wires can be fixedly mounted 90° apart at separated locations in a distal portion of the catheter to provide multi-axis, precision controlled steering. The tubular body member of the ablation catheter is constructed with sufficient columnar strength and rigidity to allow an operator to apply significant torque to the proximal end that equivalently translates to the catheters distal portions.

The present invention includes one or more systems that include the ablation catheters of the present invention. The system may further include a guide catheter such as a steerable transeptal sheath that slidingly receives the ablation catheter. The system may further include an energy delivery unit, such as a unit configured to deliver RF and/or other forms of energy to the ablation elements of the catheter. The system may further include a mapping unit that receives information recorded from one or more sensors of the ablation catheter, such as an ablation element of the ablation catheter. The mapping unit provides electrical activity information to an operator of the system. The mapping unit may be integral to the energy delivery unit.

Definitions. To facilitate an understanding of the invention, a number of terms are defined below.

As used herein, the terms "subject" and "patient" refer to any animal, such as a mammal like livestock, pets, and preferably a human. Specific examples of "subjects" and "patients" include, but are not limited, to individuals requiring medical assistance, and in particular, requiring atrial fibrillation catheter ablation treatment.

As used herein, the terms "catheter ablation" or "ablation procedures" or "ablation therapy," and like terms, refer to what is generally known as tissue destruction procedures. Ablation is often used in treating several medical conditions, including abnormal heart rhythms. It can be performed both surgically and non-surgically. Non-surgical ablation is typically performed in a special lab called the electrophysiology (EP) laboratory. During this non-surgical procedure a catheter is inserted into the heart using fluoroscopy for visualization, and then an energy delivery apparatus is used to direct energy to the heart muscle. This energy either "disconnects" or "isolates" the pathway of the abnormal rhythm (depending on the type of ablation). It can also be used to disconnect the conductive pathway between the upper chambers (atria) and the lower chambers (ventricles) of the heart. For individuals requiring heart surgery, ablation can be performed during coronary artery bypass or valve surgery.

As used herein, the term "ablation element" refers to an energy delivery element, such as an electrode for delivering electrical energy such as RF energy. Ablation elements can be configured to deliver multiple types of energy, such as ultrasound energy and cryogenic energy, either simultaneously or serially. Electrodes can be constructed of a conductive plate, wire coil, or other means of conducting electrical energy through contacting tissue. Electrodes may comprise a laminate construction, such as at least one conductive layer and at least one insulative layer. RF electrodes preferably are constructed of platinum or a combination of platinum and iridium. In monopolar energy delivery, the energy is conducted from the electrode, through the tissue to a ground pad, such as a conductive pad attached to the back of the patient. The high concentration of energy at the electrode site causes localized tissue ablation. In bipolar energy delivery, the energy is conducted from a first electrode to one or more separate electrodes, relatively local to the first electrode, through the tissue between the associated electrodes. Bipolar energy delivery results in more precise, shallow lesions while monopolar delivery results in deeper lesions. Both monopolar and bipolar delivery provide advantages, and the combination of their use is a preferred embodiment of this application. Energy can also be delivered using pulse width modulated drive signals, well known to those of skill in the art. Energy can also be delivered in a closed loop fashion, such as a system with temperature feedback wherein the temperature modifies the type, frequency and or magnitude of the energy delivered. Ablation elements may have one or more different shapes, such as tubular electrodes mounted around a shaft such as a carrier arm, and other cross-sections such as oval, triangular, rectangular and trapezoidal. Triangular cross sections can be positioned where multiple sides contact tissue for increased energy transfer or multiple sides contact a cooling source such as blood for increased cooling. The ablation elements may include a heat-sinking element, such as a projecting fin or other increased surface area portion. The ablation elements preferably include an integral temperature sensor, such as a thermocouple comprised of copper and constantan wires that are welded inside a mid portion of an RF electrode. In a preferred embodiment, an ablation element can also be used to record and map electrical activity in tissue. In an alternative embodiment, one or more ablation elements may be configured to only map electrical activity, and not be configured to deliver energy.

As used herein, the term "carrier assembly" refers to a flexible carrier, on which one or more ablation elements are disposed. Carrier assemblies include one or more carrier arms. Carrier assemblies are not limited to any particular size, or shape, and can be configured to be in expanded and unexpanded or compact states.

As used herein, the term "carrier arm" refers to a wire-like shaft capable of interfacing with electrodes and a control shaft. A carrier arm is not limited to any size or measurement. Examples include, but are not limited to: stainless steel shafts; Nitinol shafts; titanium shafts; polyurethane shafts; nylon shafts; and steel shafts. Carrier arms can be entirely flexible, or may include flexible and rigid segments.

As used herein, the term "spiral tip" refers to a carrier assembly configured in its fully expanded state into the shape of a helix or spiral. The spiral tip is not limited in the number of spirals it may contain. Examples include, but are not limited to, a wire tip body with one spiral, two spirals, ten spirals, and a half of a spiral. The spirals can lie in a relatively single plane, or in multiple planes. A spiral tip may be configured for energy delivery during an ablation procedure.

As used herein, the term "lesion," or "ablation lesion," and like terms, refers to tissue that has received ablation therapy. Examples include, but are not limited to, scars, scabs, dead tissue, burned tissue and tissue with conductive pathways that have been made highly resistive or disconnected.

As used herein the term "umbrella tip" refers to a carrier assembly with a geometric center which lies at a point along the axis of the distal portion of the tubular body member, with one or more bendable or hinged carrier arms extending from the geometric center, in an umbrella configuration. Each carrier arm may include one or more ablation elements. Each carrier arm of an umbrella tip includes a proximal arm segment and a distal arm segment, the distal arm segment more distal than the proximal arm segment when the carrier assembly is in a fully expanded condition. One or more additional carrier arms can be included which include no ablation elements, such as carrier arms used to provide support or cause a particular deflection. An umbrella tip body is not limited to any particular size. An umbrella tip may be configured for energy delivery during an ablation procedure.

As used herein, the term "carrier arm bend point" refers to a joint (e.g., junction, flexion point) located on a carrier arm. The degree of flexion for a carrier arm bend point may range from 0 to 360 degrees. The bend portion can be manufactured such what when the carrier assembly is fully expanded the bend point is positioned in a relatively straight portion, a curved portion, or in a discrete transition from a first direction to a second transition, such as a 45 degree bend transition. The bend portion can include one or more flexing means such as a spring, a reduced diameter segment, or a segment of increased flexibility.

As used herein, the term "energy delivery unit" refers to a device configured to operably attach to an ablation catheter and deliver one or more forms of energy to an ablation element. The energy delivery unit includes a user interface which allows an operator to make one or more settings involved in applying the ablative energy. The energy unit may be further configured to receive temperature information from the ablation catheter. The temperature information can provided to an operator and/or be used to provide closed loop energy delivery. The energy delivery unit may include a remote control device that may be maintained in the sterile field of the patient during the ablation procedure. The energy delivery unit may receive a signal from an operator control integral to the ablation catheter that initiates delivery of the ablation energy.

As used herein, the term "mapping unit" refers to a device configured to operably attach to an ablation catheter and receive one or more mapping signals from an ablation element or other sensor of an ablation catheter.

The present invention provides structures that embody aspects of the ablation catheter. The present invention also provides tissue ablation systems and methods for using such ablation systems. The illustrated and preferred embodiments discuss these structures and techniques in the context of catheter-based cardiac ablation. These structures, systems, and techniques are well suited for use in the field of cardiac ablation.

However, it should be appreciated that the invention is applicable for use in other tissue ablation applications such as tumor ablation procedures. For example, the various aspects of the invention have application in procedures for ablating tissue in the prostrate, brain, gall bladder, uterus, and other regions of the body, preferably regions with an accessible wall or flat tissue surface, using systems that are not necessarily catheter-based.

The multifunctional catheters of the present invention have advantages over previous prior art devices. FIGS. 1-17 show various preferred embodiments of the multifunctional catheters of the present invention. The present invention is not limited to these particular configurations.

FIG. 1 illustrates a preferred embodiment of an ablation catheter of the present invention with an umbrella tip, wherein a carrier assembly includes multiple carrier arms configured to properly engage a pulmonary vein ostium. Ablation catheter 50, and the other catheter devices of this application, are constructed of biocompatible materials suitable for percutaneous advancement through the vasculature of a patient, and for navigation within the patient's heart. Various tubular body members and shafts are constructed of extruded materials such as Pebax, silicones, polyurethanes, polymers, elastomers, flexible plastics and combinations of these. Ablation catheter 50 includes a distal tip 94, which is made of materials to be atraumatic to tissue and which is shown entering the lumen of pulmonary vein 15 such as to provide a stabilizing and/or anchoring function. Ablation catheter 50 further includes outer shaft 76 that preferably has a diameter between 8 and 9 Fr and is constructed to provide sufficient stability and torque through the procedure. Ablation catheter 50 includes a carrier assembly of the present invention, carrier assembly 85, which includes multiple ablation elements 92 mounted to distal carrier arms 88.

The ablation elements 92 and other components of carrier assembly 85 are configured to flex to conform to pulmonary vein ostia and other applicable tissues. Outer shaft 76 can be advanced forward to change the shape of carrier assembly 85 and cause one or more ablation elements 92 to contact tissue. Outer shaft 76 slidingly receives inner shaft 78, which is fixedly attached to proximal carrier arms 86. Distal carrier arms 88 are fixedly attached to distal tip 94 and the distal end of control shaft 84. Proximal carrier arms 86 are pivotally attached to distal carrier arms 88, such that advancement and retraction of control shaft 84 relative to inner tube 78 causes the diameter of carrier assembly 85 to contract and expand respectively, such as to cause the carrier assembly to expand to a 4-5 mm diameter. Inner shaft 78 further provides columnar strength to allow an operator to advance inner shaft 78 and cause carrier assembly 85 to properly contact tissue, such as to conform to non-circular pulmonary vein ostia. Inner shaft 78 preferably is attached to a pull wire (not shown), near its distal end, which is operably connected to a control on the proximal end of device 50 allowing an operator to controllably deflect the distal portion of device 50.

The distal end of outer shaft 76 includes a shaft tip 82, configured to radially expand when carrier assembly 85 is retracted. The proximal end of outer shaft 76 preferably includes a handle, not shown, but including one or more controls, such as knobs or levers, such as to advance and retract inner shaft 78 and control shaft 84. The proximal end of device 50 includes one or more connectors for connecting to an energy delivery unit and/or a mapping unit. In an alternative embodiment, one or more proximal control arms 86 are attached to a second control shaft such that the symmetry of the geometry of carrier assembly 85 can be adjusted to conform to asymmetric pulmonary vein ostia. In another alternative embodiment, device 50 is configured to be inserted over a previously placed guidewire.

Figure 2A:
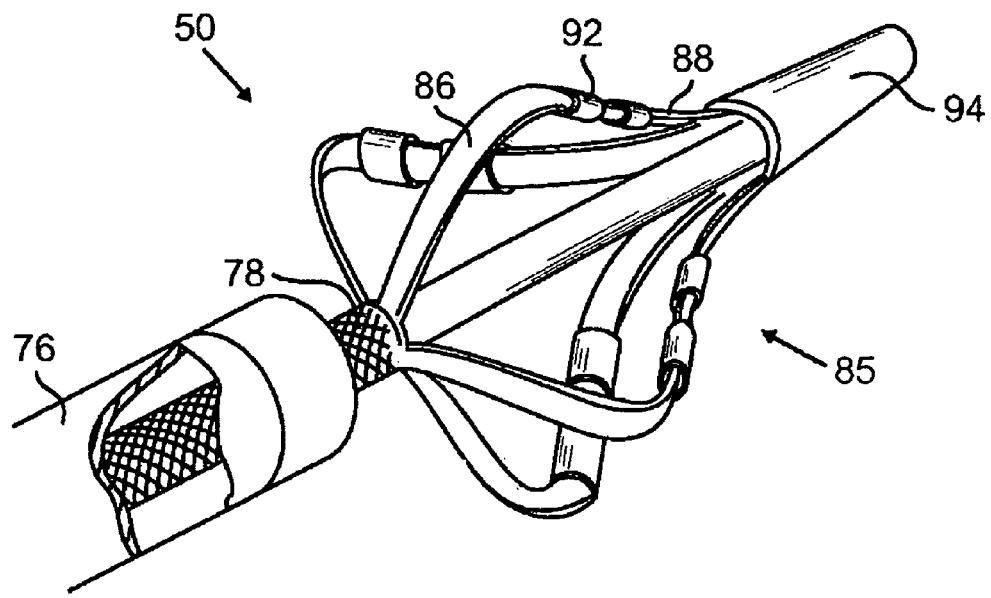
FIGS. 2a and 2b illustrates a perspective view of the distal portion of the ablation catheter of FIG. 1, consistent with the present invention.
Figure 2B:
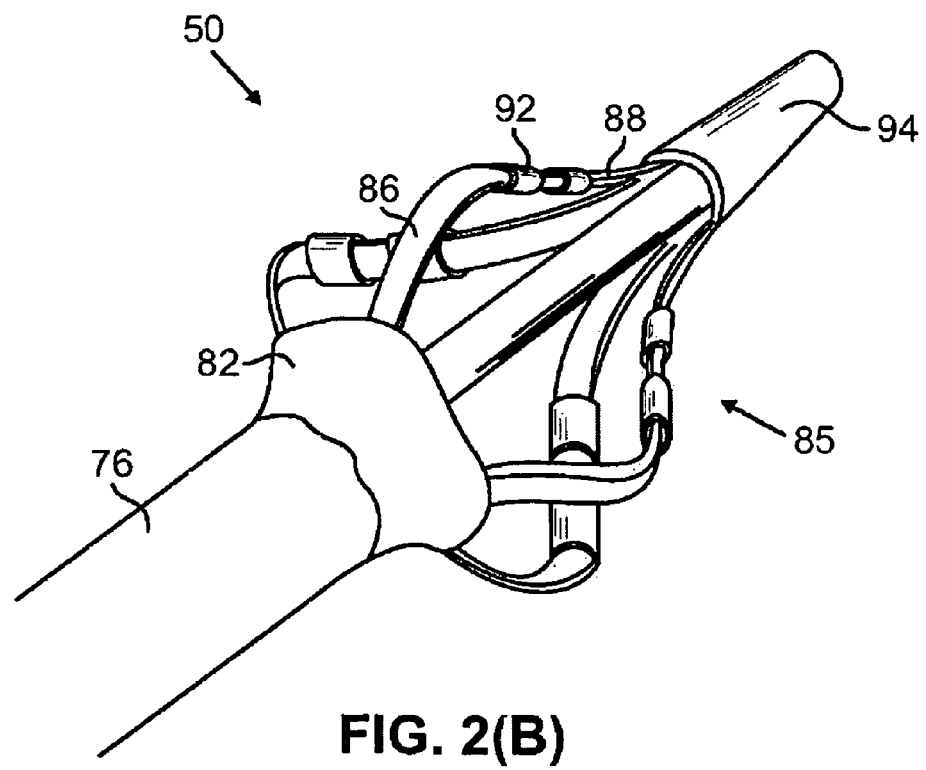

Referring now to FIGS. 2a and 2b, the distal portion of device 50 of FIG. 1 is illustrated. FIG. 2a depicts carrier assembly 85 fully expanded, with inner shaft 78 fully advanced. FIG. 2b depicts inner shaft 78 partially retracted such that proximal arms 86 are being captured and radially compressed by shaft tip 82, which expands, as shown, to create a smooth transition of carrier assembly 85 into the inner lumen of outer shaft 76.

Figure 3:
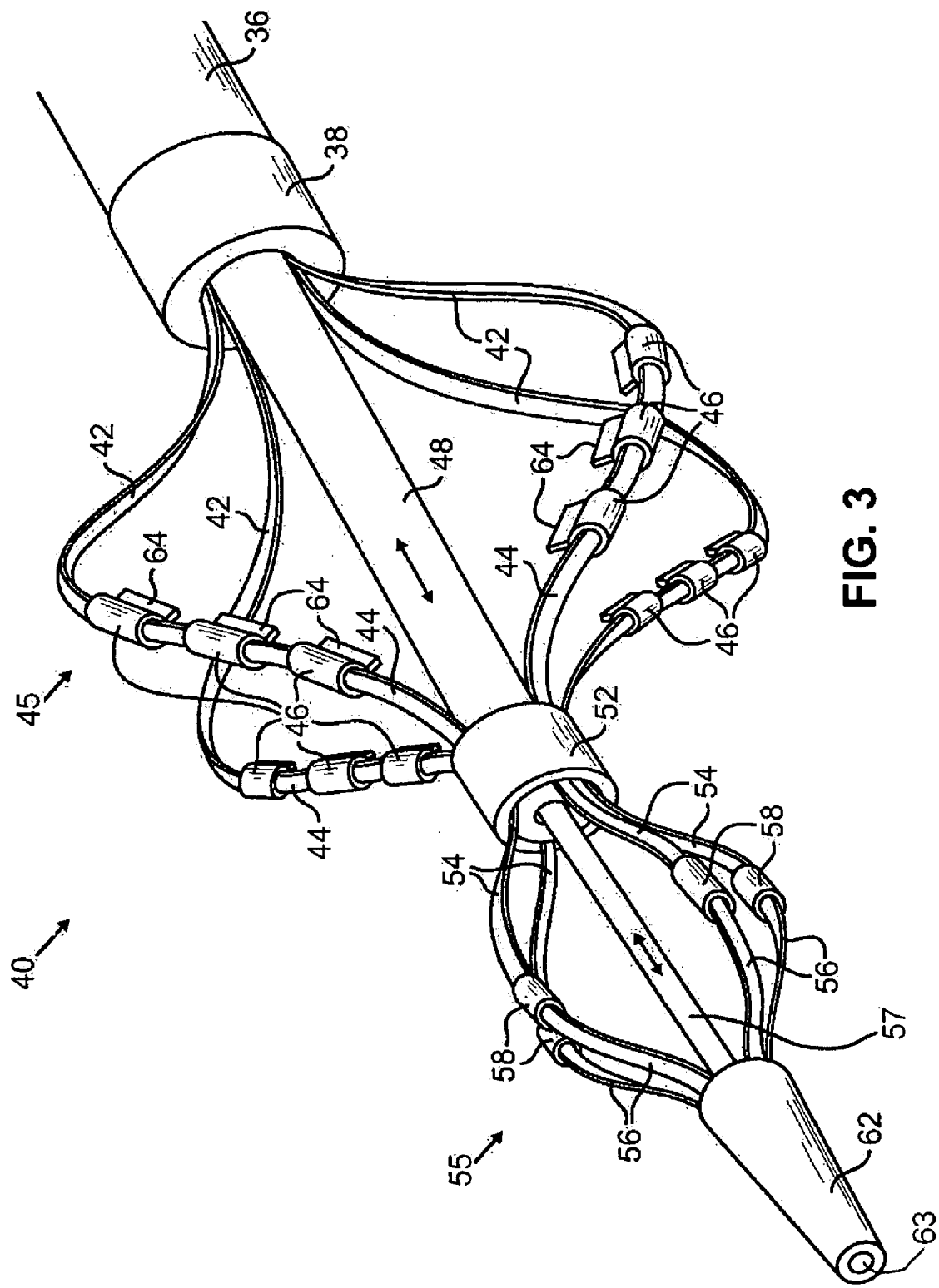
FIG. 3 illustrates a perspective view of the distal portion of an ablation catheter consistent with the present invention, in which the device includes a proximal energy delivering carrier assembly and a distal mapping carrier assembly.

Referring now FIG. 3, an ablation catheter of the present invention is illustrated comprising two carrier assemblies disposed serially along a single axis, with each carrier assembly in an umbrella tip configuration. Ablation catheter 40 includes an elongate tube, outer shaft 36, preferably constructed of Pebax material and approximately 6-8 Fr in diameter, which slidingly receives first control shaft 48. First control shaft 48 is attached on its distal portion to first carrier assembly 45, comprising multiple carrier arms and ablation elements configured to deliver energy. The proximal end of first control shaft 48, not shown, is attached to a control on the proximal end of ablation catheter 40 configured to allow an operator to precisely advance and retract first control shaft 48. First control shaft 48 includes ring 52 on its distal end that fixedly attaches one end of each distal carrier arm segment 44 to first control shaft 48. Each distal carrier arm segment 44 is pivotally attached on its opposite end to one end of a proximal carrier arm segment 42. The opposite end of each proximal arm segment 42 is fixedly attached to the distal end of outer shaft 36 via ring 38. Distal carrier arm segments 44 and proximal arm segments 42 are constructed of a flexible material, such as Nitinol, and can be resiliently biased in a straight or umbrella tip configuration. Advancement and retraction of first control shaft 48 changes the diameter of carrier assembly 45, including a fully compacted (minimal diameter) radial state when first control shaft 48 is fully advanced, and a maximum diameter state when first control shaft 48 is fully retracted.

Fixedly mounted to distal arm segments 44 are ablation elements, RF electrodes 46, configured to deliver energy to tissue to create lesions for disrupting aberrant electrical pathways in the tissue. Electrodes 46 include fins 64 configured to reside in a flow of blood during energy delivery and provide sinking of heat into the circulating blood. Electrodes 46 are configured to deliver monopolar, bipolar or a combination of monopolar and bipolar RF energy as has been described above. Electrodes 46 preferably include integral temperature sensors, such as a thermocouple welded to an internal portion of the electrode 46. Electrode 46 and any integral temperature or other sensors, are attached to wires, not shown, which travel proximally to the proximal portion of ablation catheter 40 for attachment to an energy delivery unit, a mapping unit, and/or another electronic device for sending or receiving signals and/or power.

First control shaft 48 slidingly receives second control shaft 57. Second control shaft 57 is attached on its distal portion to second carrier assembly 55, comprising multiple carrier arms and ablation elements configured to map electrical activity. The proximal end of second control shaft 57, not shown, is attached to a control on the proximal end of ablation catheter 50 configured to allow an operator to precisely advance and retract second control shaft 57. Second control shaft 57 includes tip 62 on its distal end that fixedly attaches one end of each distal carrier arm segment 56 to second control shaft 57. Tip 62 is preferably constructed of a soft or flexible material such as a soft plastic or elastomer chosen to be atraumatic to tissue, and is preferably radiopaque such as a Pebax material doped with Barium Sulfate. Distal tip 62 is constructed to help navigation into and stabilization within a pulmonary vein. Distal tip 62 includes guidewire lumen 63, which is in fluid communication with an internal lumen of second control shaft 57, the lumen traveling to and exiting a proximal portion of ablation catheter 40, such that ablation catheter 40 can be percutaneously inserted into the vasculature of a patient over a guidewire.

Each distal carrier arm segment 56 is pivotally attached on its opposite end to one end of a proximal carrier arm segment 54. The opposite end of each proximal arm segment 54 is fixedly attached to the distal end of first control shaft 48 via ring 52. Distal carrier arm segments 56 and proximal arm segments 54 are constructed of a flexible material, such as Nitinol, and can be resiliently biased in a straight or umbrella tip configuration. Advancement and retraction of second control shaft 57 changes the diameter of carrier assembly 55, including a fully compacted (minimum diameter) radial state when second control shaft 57 is fully advanced, and a maximum diameter state when second control shaft 57 is fully retracted.

Fixedly mounted to distal arm segments 44 are ablation elements, mapping electrodes 58, configured to map electrical activity present in tissue to target areas for creating lesions and/or otherwise assess a patient condition. Electrodes 58 are constructed of a conductive material such as platinum or a combination of platinum and iridium. Electrodes 58 preferably include integral temperature sensors, such as a thermocouple welded to an internal portion of the electrode 58. Electrode 58 and any integral temperature or other sensors, are attached to wires, not shown, which travel proximally to the proximal portion of ablation catheter 40 for attachment to a mapping unit, an energy delivery unit, and/or another electronic device for sending or receiving signals and/or power.

Figure 4:
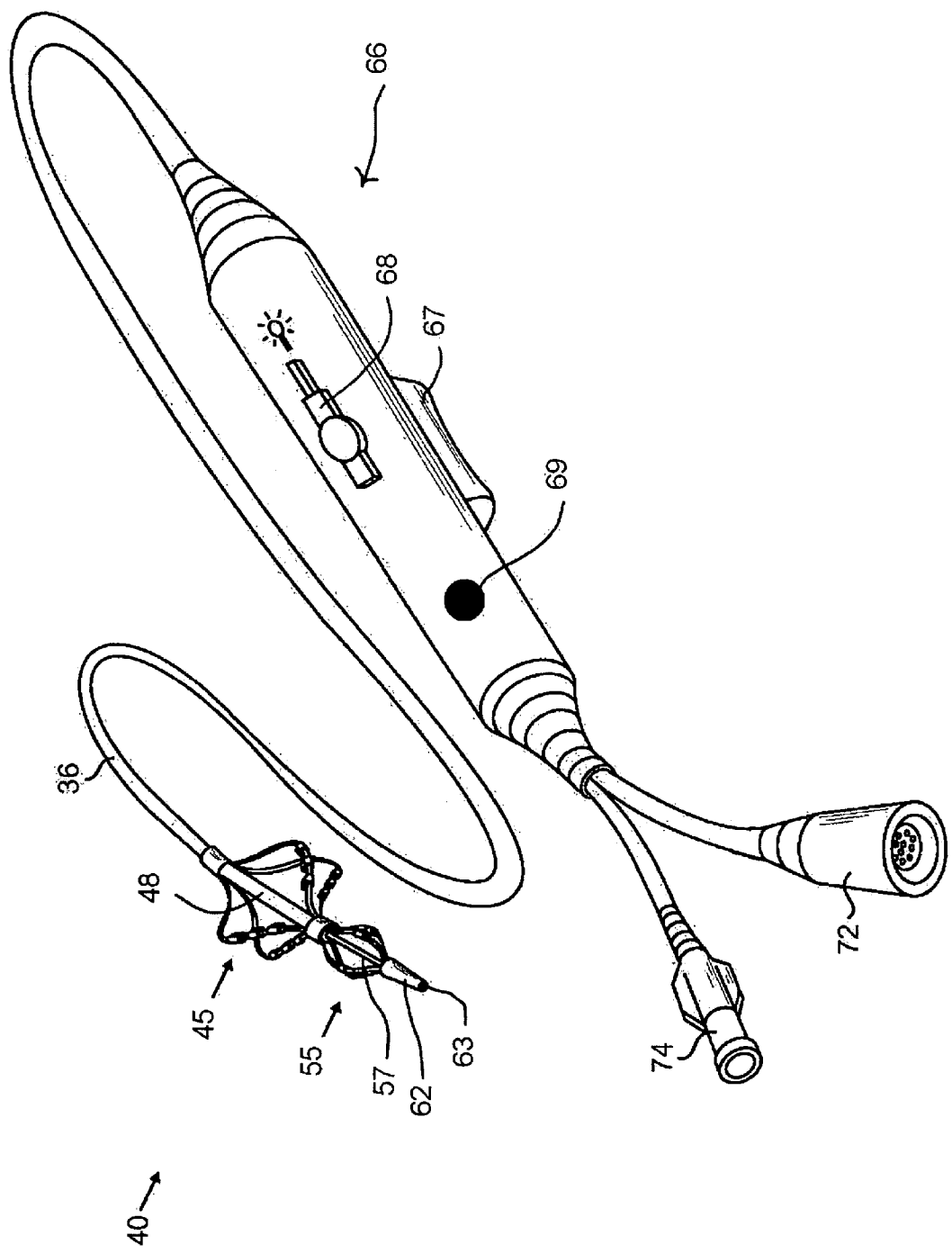
FIG. 4 illustrates an ablation catheter handle consistent with the present invention including the dual carrier assemblies of FIG. 3.

Ablation catheter 40 of FIG. 3 includes on its proximal end, a handle, not shown, but preferably of the type described in reference to FIG. 4 and including multiple controls for allowing an operator to: advance and retract first control shaft 48; advance and retract second control shaft 57; activate energy delivery to one or more of electrodes 46 or 58; operate a user interface of an energy delivery unit or mapping unit (both not shown); or perform another function. The handle includes an exit port through which a guidewire, such as a guidewire that has been placed into a pulmonary vein of the patient, can exit. Carrier assembly 55 is sized such that it can engage the luminal wall of a pulmonary vein, and carrier assembly 45 is sized and of sufficient flexibility such that it can engage the ostium of a pulmonary vein, including a non-circular orifice. Outer shaft 36 is constructed of sufficient material and the handle may be manipulated to apply conforming forces to carrier assembly 55 and/or carrier assembly 45. Both first control shaft 48 and second control shaft 57 are configured to transmit sufficient torque to allow an operator to precisely rotationally position carrier assembly 45 and carrier assembly 55 respectively.

In an alternative embodiment, the ablation elements 46 of proximal carrier assembly 45 may be configured to additionally or alternatively map electrical activity in tissue. In another alternative embodiment, the ablation elements 58 of distal carrier assembly 55 may be configured to additionally or alternatively delivery ablation energy such as RF energy. In another alternative embodiment, the carrier arms of carrier assembly 45 and/or carrier assembly 55 may include sensors, such as temperature thermocouples, placed within an electrode or mounted to a carrier arm some distance from an electrode, such as midway between two electrodes. Ring 38 and Ring 52 are preferably made of a compressible material, such as a metal which can be crimped in a manufacturing process. In an alternative or additional embodiment, adhesives may be used to fixed one or more carrier arms to a shaft. One or more adhesives may be used to attach distal tip 62.

Referring Now to FIG. 4, an ablation catheter of the present invention is illustrated including the dual carrier assemblies of the ablation catheter of FIG. 3. Ablation catheter 40 includes a tubular body member, outer shaft 36, which includes on its distal end, proximal carrier assembly 45 and distal carrier assembly 55, as have been described in detail in reference to FIG. 3. The proximal end of outer shaft 36 is attached to handle 66, which includes multiple controls: slide 67, slide 68 and button 69. Slide 67 is operably attached to first control shaft 48. Slide 68 is operably attached to second control shaft 57. Movement of slides 67 and 68 change the geometries of first carrier assembly 45 and second carrier assembly 55 as has been described in detail in reference to FIG. 3. Numerous types of mechanical mechanisms can be incorporated into handle 66 to operably advance one or more control shafts, such as linear slides, rotating knobs or rotating levers such as knobs connected to cam assemblies, and other mechanisms used to move the shafts forward and back. Button 69 is used to initiate energy delivery, such as when first carrier assembly 45 is positioned against a pulmonary vein ostium and ablation catheter 40 is electrically connected to an energy delivery unit, not shown.

Handle 66 includes two pigtails, one which terminates in luer 74 and the other which terminates with electrical connector 72. Luer 74 is in fluid communication with guidewire lumen 63 exiting tip 62 such that ablation catheter 40 can be advanced over-the-wire into the vasculature of the patient. Electrical connector 72 includes multiple connection points for multiple wires that travel within outer shaft 36 and connect to ablation elements and one or more sensors such as temperature sensors included in first carrier assembly 45 and second carrier assembly 55. Electrical connector 72 is configured to electrically connect to one or more of: an energy delivery unit; a mapping unit; an electronic device for receiving and/or transmitting signals and/or power such as signals received from temperature or other physiologic sensors of ablation catheter 40; and combinations of these.

Figure 5:
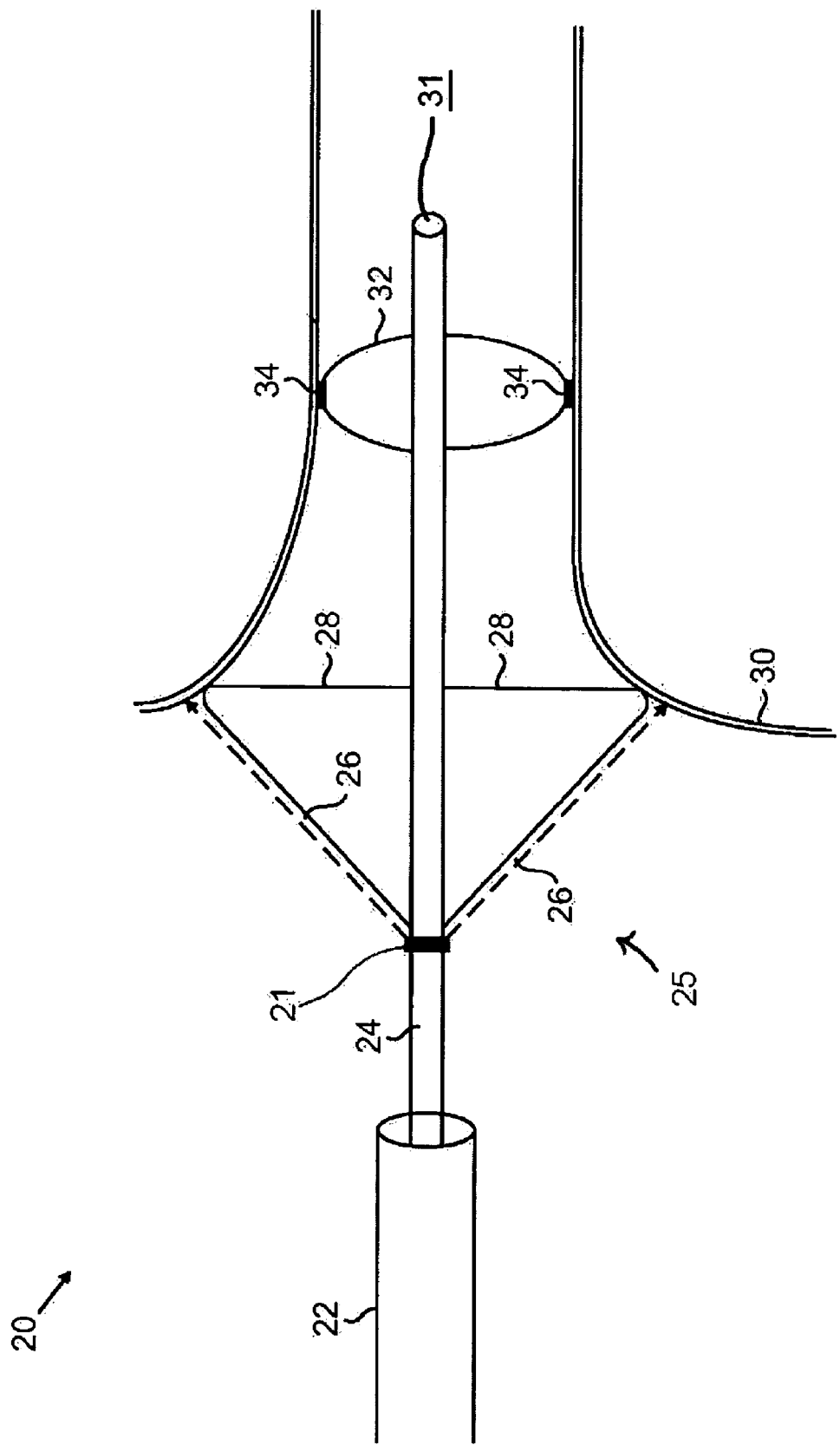
FIG. 5 illustrates a side sectional view of an ablation catheter, consistent with present invention, with the distal end inserted into a pulmonary vein of a patient.

Referring now to FIG. 5, an ablation catheter of the present invention is illustrated wherein an ultrasound crystal forwardly directs ultrasonic energy in a circular pattern. Ablation catheter 20 includes outer shaft 22, which slidingly receives control shaft 24, both of which have similar construction to the tubular body members and other shafts described throughout this application. Mounted to control shaft 24 is carrier assembly 25, comprising proximal carrier arms 26 and distal carrier arms 28. Proximal carrier arms 26 and distal carrier arms 28 are made of a flexible material such as Nitinol wire and may be resiliently biased in the geometry shown or a different geometry such as a radially compact geometry compatible with intravascular insertion. Each proximal carrier arm 26 is fixedly attached at one end to control shaft 24. Each proximal carrier arms 26 is pivotally attached at its opposite end to an end of distal carrier arms 28. The opposite end of each distal carrier arm 28 is fixedly attached, at a location more distal, to control shaft 24, such that a right-angle construction is achieved. A first proximal arm 26 and attached distal arm 28 pair is attached 180° from a second proximal arm 26 and attached distal arm 28 pair, as shown in FIG. 5. The two pairs are used to contact pulmonary vein ostium 30, also as shown. Additional carrier arm pairs may be included, such as a total of four pairs separated by 90°.

Distal to distal carrier arms 28, are centering arms 32, configured to center control shaft 24 in the pulmonary vein ostium and/or stabilize the distal portion of ablation catheter 20 such as during delivery of ablation energy of mapping of electrical activity. Centering arms 32 are of similar construction to carrier arms 26 and 28, such as a round or flat Nitinol band. Alternatively or in addition to centering arms 32, the distal portion of control shaft 24 may include an inflatable balloon configured to center and/or anchor control shaft 24. The centering balloon, not shown, may include one or more mapping and/or energy delivery elements. The centering and/or stabilizing elements of ablation catheter 20, such as the centering arms 32, an inflatable balloon, or other similarly functioning element, may be integrated into the other ablation devices and catheters described throughout this application. These stabilizing and centering elements are particularly useful when accessing pulmonary vein ostia that are non-circular.

Fixedly mounted to centering arms 32 are mapping elements 34, electrodes configured to record electrical activity found in tissue. Control shaft 24 includes guidewire lumen 31, which exits the distal end of control shaft 24 and travels proximally and exits a proximal portion of ablation catheter 20. In a preferred method, ablation catheter 20 is advanced over a previously placed guidewire that has its distal end placed into a pulmonary vein of the patient.

Fixedly mounted to control shaft 24 is ultrasound crystal 21, a tubular energy delivery element configured to deliver ultrasonic energy along a cone shaped path, such as along the trajectory of proximal carrier arms 26 (dashed lines shown on FIG. 5). The vector of energy delivery will cause a relatively circular patterned lesion around the pulmonary vein ostium. In an alternative embodiment, the ultrasound crystal may be configured to provide energy in a sector (less that 360°), and the carrier assembly 25 would be rotated and repositioned by an operator between ablations to sequentially create a full circumferential lesion.

Advancement and retraction of control shaft 24 can be used to change the diameter of carrier assembly 25, such as retraction wherein the proximal portion of carrier assembly 25 is captured within the lumen of outer shaft 22. Centering arms 32 are preferably connected to a control shaft, not shown, such that the centering arms can be expanded and contracted. In alternative embodiments with centering and/or stabilizing balloons, or other similar functional elements, the size of the element is configured to be controlled (e.g. expanded and contracted) from the proximal end of the ablation catheter.

Figure 6:
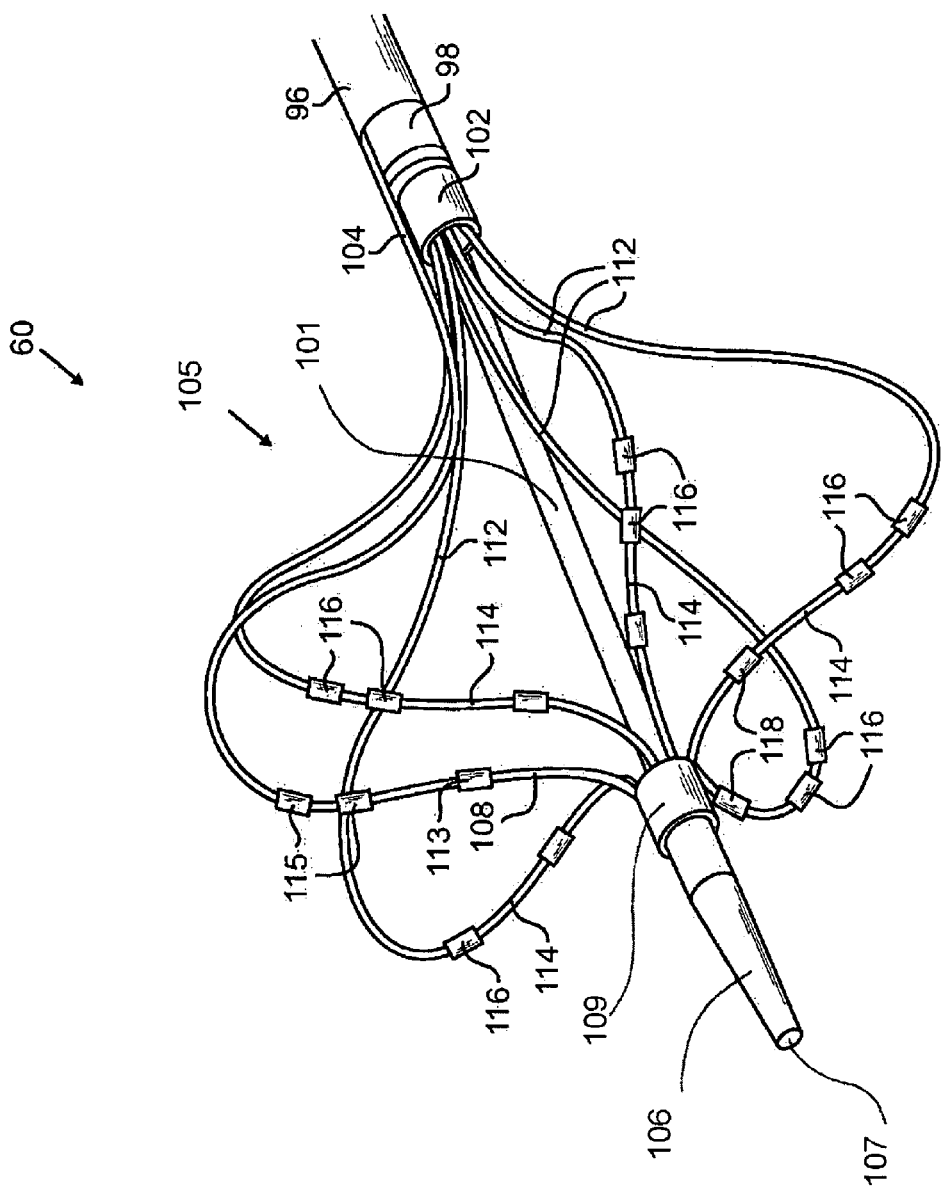
FIG. 6 illustrates a perspective view of the distal portion of an ablation catheter consistent with the present invention, in which the carrier assembly includes one or more carrier arms that can be rotationally positioned.

Referring now to FIG. 6, an ablation catheter of the present invention is illustrated wherein one or more carrier arms can be rotated along the axis of the distal portion of the outer shaft. Ablation catheter 60 includes outer shaft 96, ring 98, ring 102, carrier assembly 105, ring 109 and tip 106, all of which include similar components, materials, construction and function to the same or like parts used in reference to the ablation catheters described hereabove. Carrier assembly includes multiple proximal carrier arms 112 which are each at one end fixedly attached to ring 102. Proximal carrier arms 112 are each pivotally attached at their opposite end to one end of distal carrier arms 114. The opposite end of each distal carrier arms 114 is fixedly attached to control shaft 101 via ring 109, such that advancement of control shaft 101 relative to outer shaft 96 causes carrier assembly 105 to change shape. Full advancement of control shaft 101 causes carrier assembly 105 to transition to a compact, minimum diameter configuration, and retraction of control shaft 101 causes carrier assembly 105 to transition to a maximum diameter configuration, such as for contacting pulmonary vein ostia.

Carrier assembly 105 further includes a rotatable arm comprising distal arm segment 108 and proximal arm segment 104. One end of distal arm segment 108 is rotatably attached to control shaft 101 via ring 109. The opposite end of distal arm segment 108 is pivotally attached to proximal arm segment 104. The opposite end of proximal arm segment 104 is fixedly attached to ring 98, which in turn is fixedly attached to a control shaft, not shown but continuing proximally to a control (such as a lever or knob on a handle, both not shown) configured to allow an operator to precisely rotate carrier arm 104.

The distal end of control shaft 101 includes tip 106, which is preferably made of flexible material to be atraumatic to tissue. Tip 106 includes a guidewire lumen 107 which continues proximally and exits a proximal portion of ablation catheter 60 such that ablation catheter 60 can be percutaneously advanced over a previously placed guidewire, such as a guidewire placed into a pulmonary vein as has been described hereabove.

Each distal carrier arms 114 includes multiple ablation elements 116 configured to deliver energy to tissue. Distal to the ablation elements 116 is mapping element 118 configured to record electrical signals present in tissue. Distal carrier arm 108 includes multiple ablation elements 115 configured to deliver energy to tissue. Distal to the ablation elements 115 is mapping element 113 configured to record electrical signals present in tissue. Proximal carrier arm 104 can be rotated and remain concentric with the static carrier arms, such that the ablation elements 115 on distal arm segment 108 can be positioned at a specific distance from one or more of the ablation elements 116 on static distal carrier arms 114. The positioning through rotation can be used to achieve lesions of a specific length or other property, especially when bipolar energy is transmitted between ablation element 115 and one or more ablation elements 116. This configuration provides simplified use in creating continuous lesions created one sector at a time. The rotation of proximal arm segment 104 and distal arm segment 114 can also be performed to more properly match the contour of a non-circular pulmonary vein ostium.

In an alternative embodiment, ablation catheter 60 includes multiple rotatable carrier arms, such as carrier arms connected to independent or ganged control shafts such that multiple carrier arms and their integral ablation element can be rotated to modify the carrier assembly geometry.

Figure 7:
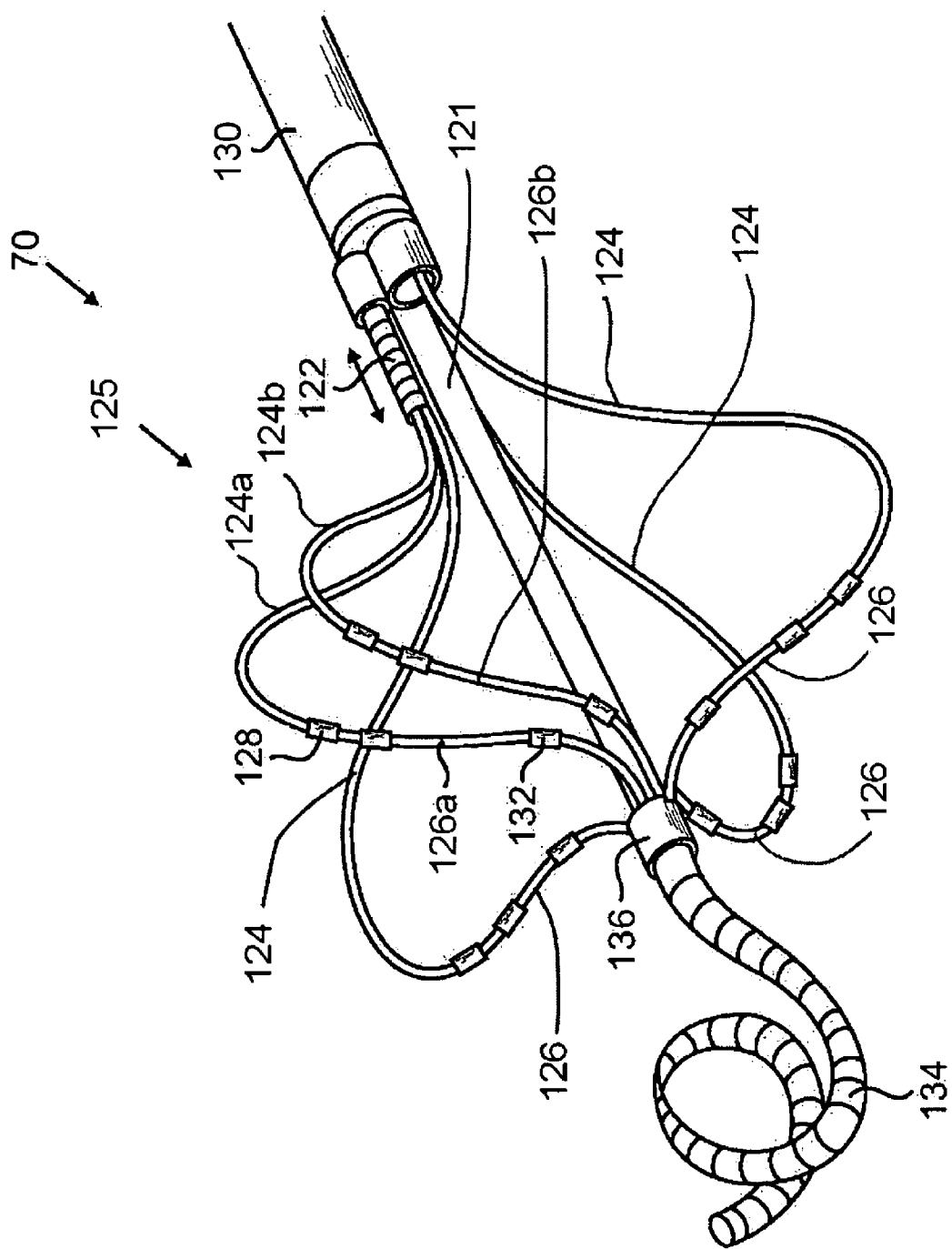
FIG. 7 illustrates a perspective view of the distal portion of an ablation catheter consistent with the present invention, in which a sleeve can be advanced to manipulate one or more carrier arms of the carrier assembly, and the distal end includes a flexible wire for inserting into a pulmonary vein.

Referring now to FIG. 7, an ablation catheter is illustrated with a carrier assembly including multiple carrier arms, some of which can be repositioned relative to other carrier arms. Ablation catheter 70 includes outer shaft 130, first control shaft 121, second control shaft 122, carrier assembly 125 and ring 136, all of which include similar components, materials, construction and function to the same or like parts used in reference to the ablation catheters described hereabove. Carrier assembly 125 includes multiple carrier arms comprising proximal arm segments 124, 124*a* and 124*b*, each of which are pivotally attached to distal arm segments 126, 126*a* and 126*b* respectively. Proximal arm segments 124 and distal arm segments 126, 126*a* and 126*b* are fixedly attached on their opposite ends, as has been described hereabove, such that advancement and contraction of control shaft 121 decreases and increases the diameter of carrier assembly 125, respectively.

Ablation catheter 70 further includes second control shaft 122 which is hollow at least on its distal portion and surround proximal arm segments 124*a* and 124*b* such that advancement of control shaft 122 causes proximal arm segments 124*a* and 124*b*, each of which includes ablation elements 128 and mapping element 132, to move towards each other, changing the geometry of carrier assembly 125, similar to the geometry change causes by rotating a carrier arm as was described in reference to FIG. 6. Both control shaft 121 and control shaft 122 are preferably operably connected to a control such as a knob or lever in a handle on the proximal end of ablation catheter 70. Repositioning of one or more carrier arms may be performed to increase or decrease the distance between ablation elements, mapping electrodes or other arm-mounted sensors or transducers. Repositioning of the arms may also be performed to better conform to various pulmonary vein anatomies, such as pulmonary veins with non-circular ostia.

Ablation device 70 of FIG. 7 further includes an elongate floppy tip 134, preferably of a guidewire-like construction, to assist in entering an orifice such as a pulmonary vein lumen, or in maintaining stability during a mapping or ablating procedure. In an alternative embodiment, ablation device 70 includes a guidewire lumen from a proximal portion of the device to a distal portion of the device.

Figure 8A:
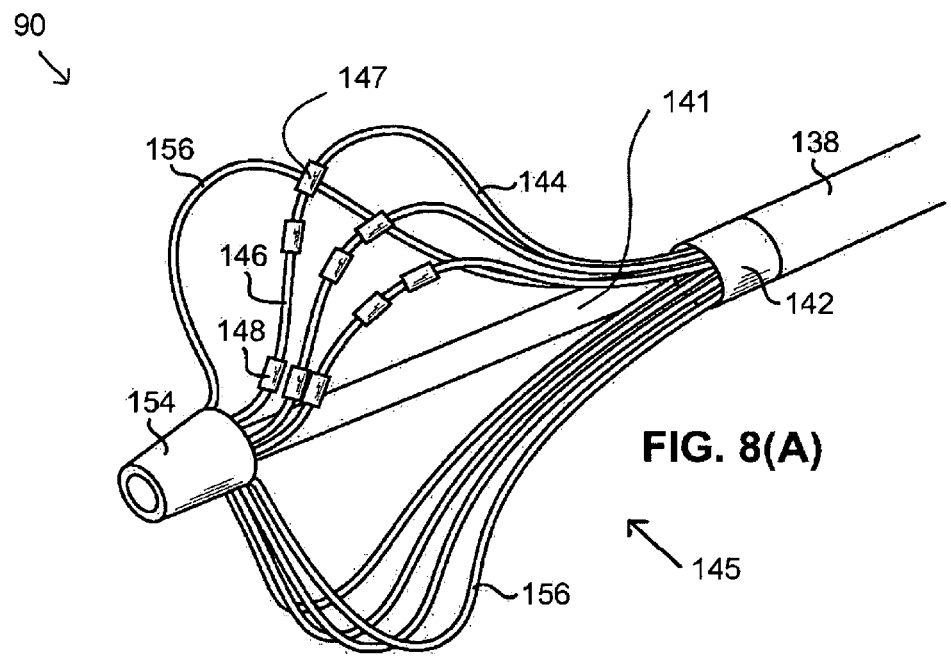
FIG. 8a illustrates a perspective view of the distal portion of an ablation catheter consistent with the present invention, in which one or more carrier arms of the carrier assembly are maintained in close proximity with a collar.

Referring now to FIG. 8*a*, an ablation catheter of the present invention is illustrated in which multiple carrier arms are maintained in fixed positions by a ring, such as an advancable ring. Ablation catheter 90 includes outer shaft 138, control shaft 141, carrier assembly 145 and tip 154, all of which include similar components, materials, construction and function to the same or like parts used in reference to the ablation catheters described hereabove. Carrier assembly 145 includes proximal arm segments 144 which are pivotally attached to distal arm segments 146. Each distal arm segment 146 includes multiple ablation electrodes 147 and a mapping sensor 148 distal to the ablation electrodes 147. Carrier assembly 145 further includes multiple carrier arms 156, which may be void of electrodes as shown, or may include one or more mapping or ablating electrodes, or other sensor or transducer.

Figure 8B:
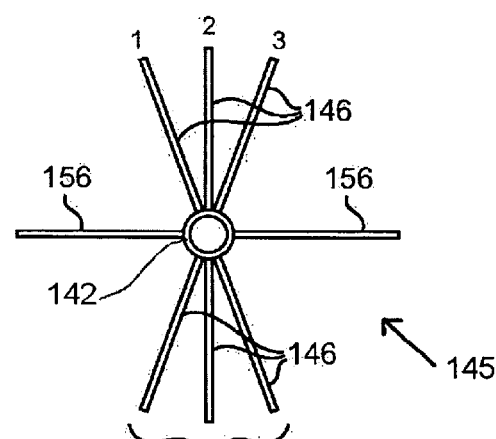
Figure 8C:
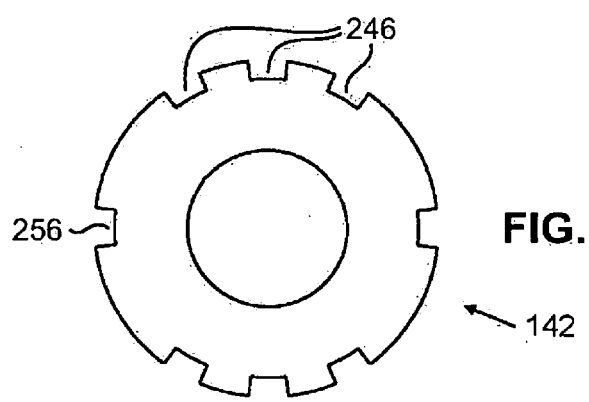

Referring also to FIG. 8*c*, each proximal carrier arm segment is circumferentially positioned in a groove 246 of ring 142. Carrier arms 156 are similarly positioned in a groove 256 of ring 142. Ring 142 is preferably attached to a control shaft, not shown, such that advancement of that control shaft changes the geometry of carrier assembly 145 accordingly. Retraction of control shaft 141 changes the diameter of carrier assembly 145 as has been described in detail hereabove. FIG. 8*b* illustrates an end view of the ablation catheter 90 of FIG. 8*a*, showing the rotational orientation of the distal arm segments 146 and carrier arms 156. Carrier arms 156 are positioned orthogonal to two sets of three distal carrier arms 146 such as to provide positioning and radial support to distal carrier arms 146. Various configurations of carrier arm geometries can be provided for handling of various pulmonary vein tissue contours. Ring 142 may maintain the ablation elements 147 and/or the mapping elements 148 in close proximity.

In an alternative embodiment, ring 142 is not advancable (not connected to a control shaft), but included with grooves 256 and grooves 246 to maintain the rotational orientation of the distal carrier arms 146 and the carrier arms 156 such as when force is applied to outer shaft 138, such as via a handle, the force translated to carrier assembly 145.

Figure 9:
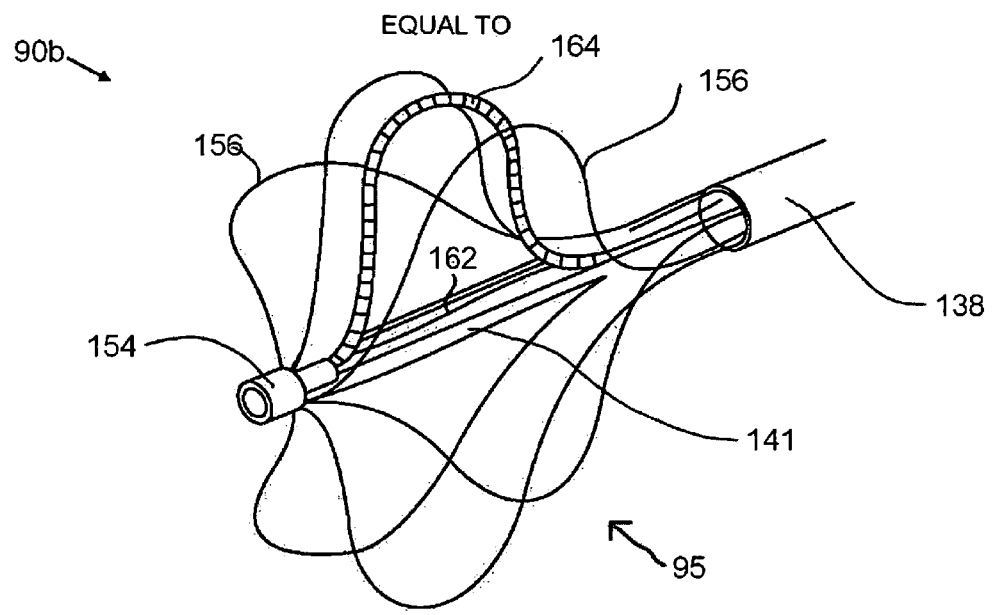
FIG. 9 illustrates a perspective view of the distal portion of an ablation catheter consistent with the present invention, in which the carrier assembly includes a radially deployable spline that can be deployed in between two carrier arms.
Figure 9A:
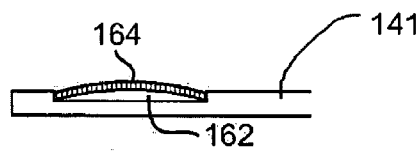
FIGS. 9a and 9b illustrate a side view of the distal portion of the ablation catheter of FIG. 9a, with the spline in partially and fully deployed conditions, respectively, with the carrier arms removed for clarity.
Figure 9B:
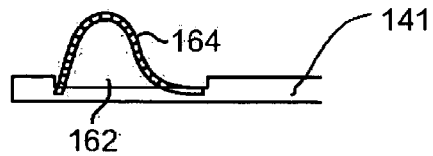

Referring now to FIG. 9, an ablation catheter of the present invention is illustrated in which an advancable spline can be radially expanded to improve or otherwise alter the structure and rigidity of a carrier assembly. Ablation catheter 90*b* includes outer shaft 138, control shaft 141, carrier assembly 95 and tip 154, all of which include similar components, materials, construction and function to the same or like parts used in reference to the ablation catheters described hereabove. Carrier assembly 95 includes multiple carrier arms 156 in an umbrella tip configuration, one or more including ablation elements, other sensors or transducers, all not shown. As control shaft 141 is advanced and retracted (e.g. via a control on a proximal handle, both not shown), carrier assembly 95 contracts and expands respectively, as has been described hereabove. Control shaft 141 slidingly receives an advancable spline 164, whose distal end resides in recess 162 of control shaft 141. Advancement of spline 164 causes its distal end to extend radially out from control shaft 141 as is shown in FIG. 9*a* (partially extended) and FIG. 9*b* (fully extended). In a preferred embodiment, spline 164 can be advanced to the maximum diameter of carrier arms 156. In an alternative embodiment, spline 164 can be advanced to a diameter greater than the maximum diameter of carrier arms 156. Spline 164 is advance to modify the performance characteristics of carrier assembly 95, such as to modify the supporting forces applied to tissue. In an alternative embodiment, spline 164 includes one or more ablation elements (e.g. RF electrodes) or other sensors or transducers.

Figure 10:
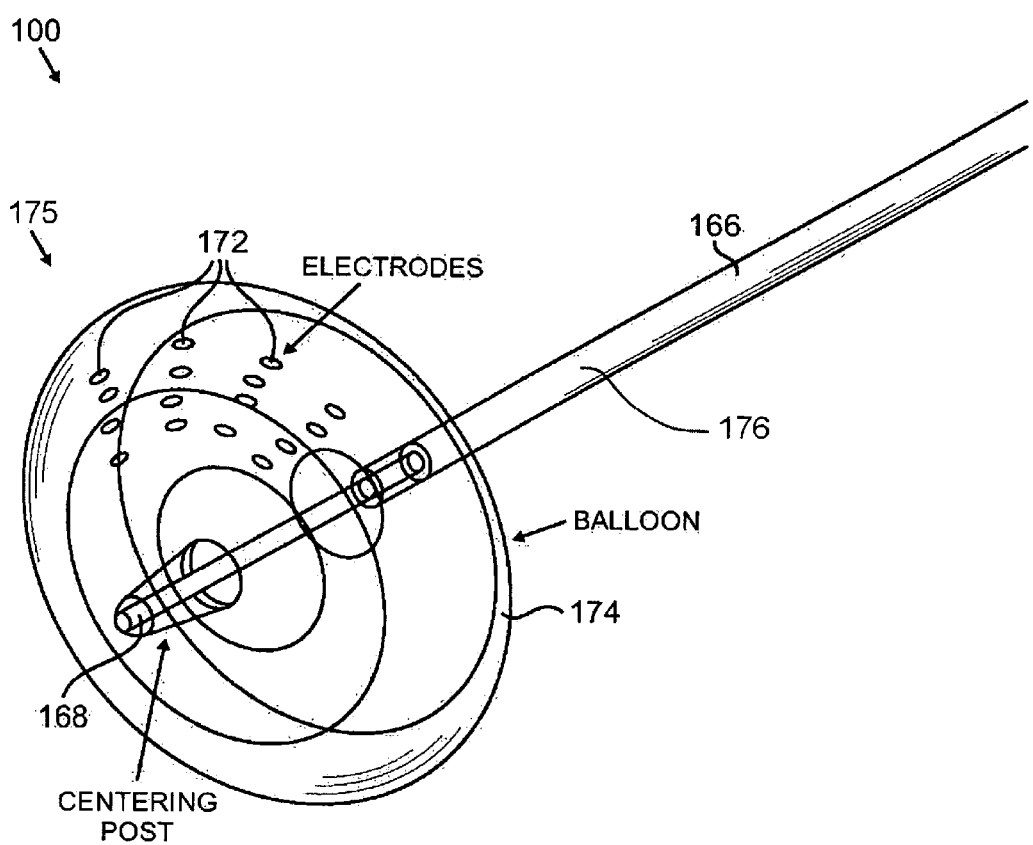
FIG. 10 illustrates a perspective view of the distal portion of an ablation catheter consistent with the present invention, in which the carrier assembly comprises a balloon with fixedly mounted ablation elements.
Figure 11:
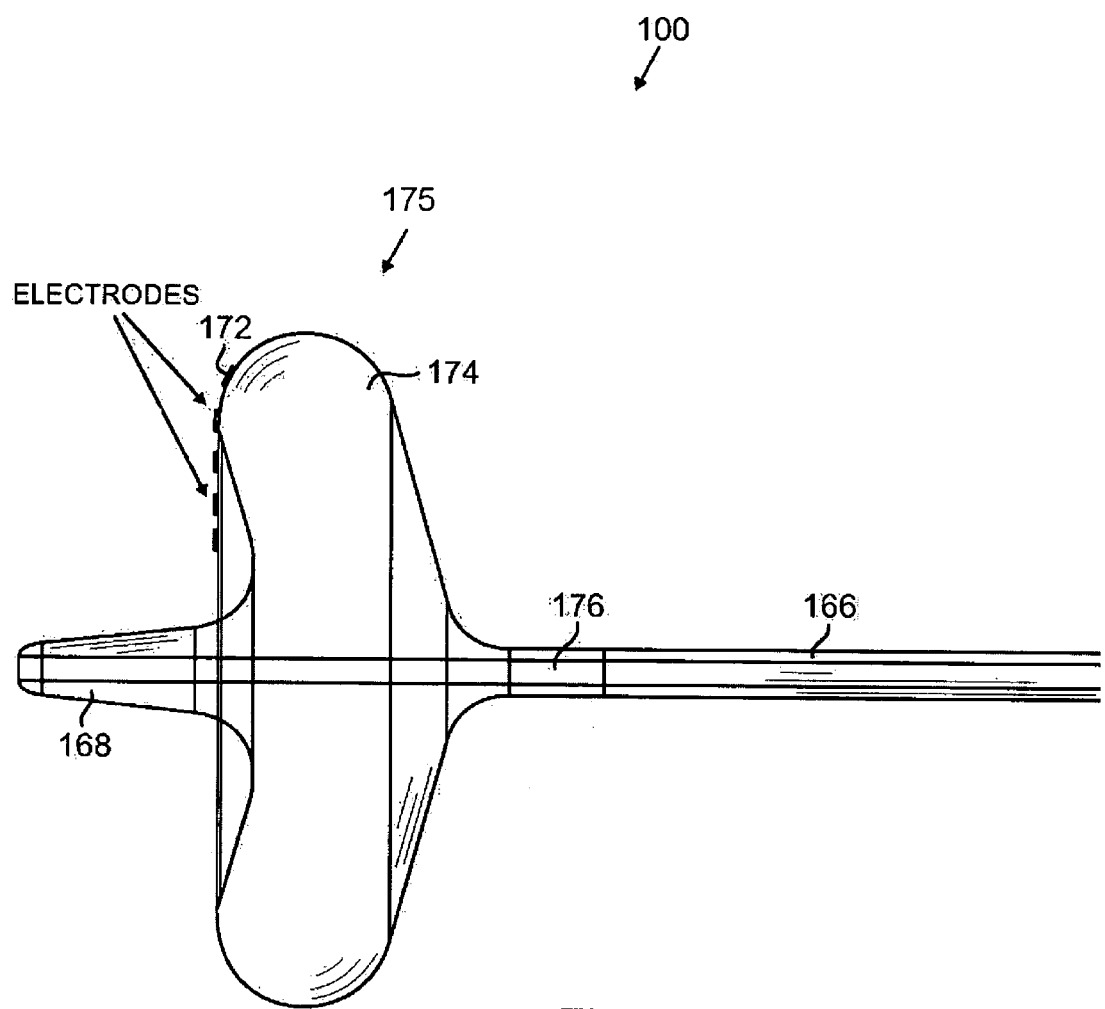
FIG. 11 illustrates a side view of the distal portion of the ablation catheter of FIG. 10.

Referring now to FIGS. 10 and 11, an ablation catheter of the present invention is illustrated in which the carrier assembly comprises an inflatable balloon with multiple ablation elements mounted on or embedded in its external surface. Ablation catheter 100 includes carrier assembly 175 comprising balloon 174 and electrodes 172, such as RF ablation or electrical signal mapping electrodes. Ablation catheter 100 further includes an elongate tubular body, outer shaft 166, which includes an inflation lumen 176 from its proximal portion to the inner cavity of balloon 174. Balloon 174 is sealed and fixedly attached to the distal portion of outer shaft 166. Passage of fluid such as air or saline through the inflation lumen of outer shaft 166 causes balloon 174 to inflate and remain in an expanded state as long as the fluid pressure is maintained. Balloon 174 may be a compliant or non-compliant balloon, and while shown as a disk or donut shape, may have profiles specific to mimic pulmonary vein ostia and the tissue extending therefrom.

Extending from the distal end of and coaxial to external shaft 166 is centering post 168 which traverses from the proximal end to the distal end of balloon 174, and includes a projection configured to engage a pulmonary vein lumen. In a preferred embodiment, a guidewire lumen is included from the distal end to a proximal portion of ablation catheter 100 such that ablation catheter may be advanced over a guidewire such as a guidewire that has previously been placed into a pulmonary vein ostium or other applicable orifice. Mapping and/or ablating procedures can be accomplished by an operator applying a force to balloon 174 via shaft 166, and transmitting ablation energy to electrodes 172 and/or recording electrical activity from electrodes 172.

Figures 12A, 12B, 12C:
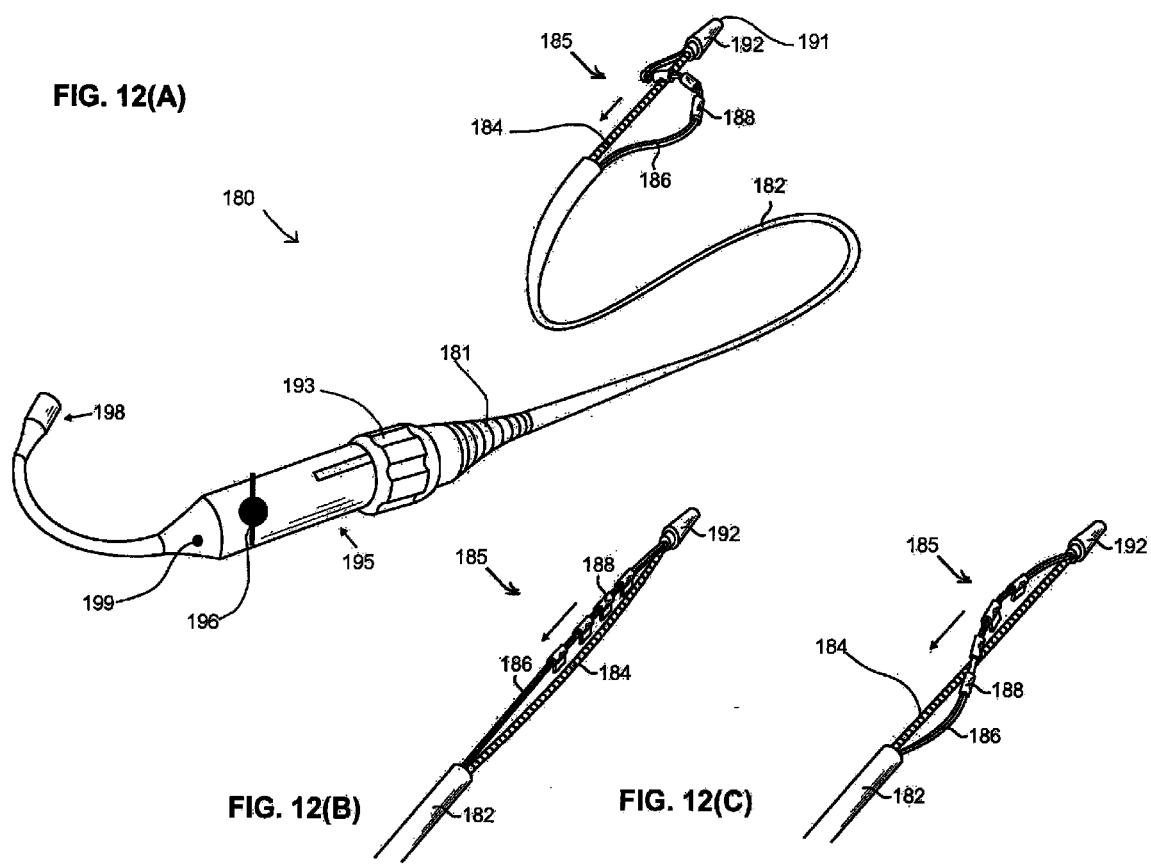
FIG. 12a illustrates a perspective view of an ablation catheter consistent with the present invention, wherein the carrier assembly comprises a single carrier arm and the carrier assembly is in the deployed state.
FIG. 12b illustrates a perspective view of a distal portion of the ablation catheter of FIG. 12a, in which the carrier assembly is in a fully compacted state.
FIG. 12c illustrates a perspective view of a distal portion of the ablation catheter of FIG. 12b, in which the carrier assembly is in a partially deployed state.

Referring now to FIG. 12*a*, ablation catheter of the present invention is illustrated in which the carrier assembly includes a single carrier arm that can be positioned into an adjustable, partial circumferential (less than 360°) loop for ablating and/or mapping tissue. Ablation device 180 includes an elongate tubular body member, outer shaft 182, with sufficient column and torsion strength to support standard interventional procedures such as those which access the vasculature from a femoral vein or artery and access the patient's heart. Outer shaft 182 is constructed of biocompatible materials such as Pebax, and preferably includes an inner braid, such as a stainless steel 304 braid. The proximal portion of outer shaft 182 is preferably made of Pebax 7233D and the distal portion of outer shaft 182 is preferably made of Pebax 55/3533D. Outer shaft 182 is fixedly attached to handle 195 via strain relief 181.

Exiting the distal end of cater shaft 182 are control shaft 184 and carrier assembly 185, which comprises a single carrier arm 186. At least one of control shaft 184 and carrier arm 186 can be advanced and/or retracted by manipulating a control on handle 195, such as rotating knob 193. In a preferred embodiment, the proximal end of carrier arm 186 is fixedly attached to a distal portion of outer shaft 182, such as via a crimp and/or adhesives, and control shaft 184 is slidingly received by outer shaft 182 and operably attached to rotating knob 193. Carrier assembly 185, preferably made of an elastic material such as Nitinol covered with a sleeve made of Pebax, includes one or more electrodes 188 along its length. The electrodes 188 may include heat-sinking fins as shown. The electrodes 188 are preferably made of platinum, and are typically 3 mm long and separated by 1 to 4 mm, with symmetric or asymmetric spacing. Four electrodes 188 are depicted in FIGS. 12*a* through 12*c*. Four (4) to sixteen (16) electrodes 188 are preferred, typically eight (8) to ten (10). The presence of multiple, typically uniformly distributed electrodes enables the operator to rapidly identify problematic target areas (undesired electrical activity) and create lesions (ablate) rapidly. The multi-electrode geometry of carrier assembly 185, precision loop control, and ease of positioning (including over-the-wire positioning and anchoring), enables simplified, customized diagnosis and treatment of heart rhythm disorders such as atrial fibrillation.

Electrodes 188 may be for delivering of ablation energy, for mapping of electrical activity, and/or for performing other functions such as pacing of the heart. Alternatively or additionally, carrier assembly 185 may include different types of sensors and/or transducers, such as sensors or transducers that can be applied to the ostium of a vessel to perform a diagnostic and/or therapeutic function. The distal end of carrier arm 186 is fixedly attached to the distal end of control shaft 184, the connection point encased by tip 192. Tip 192 is of materials and construction to be atraumatic, such as a Pebax tip, which has been doped with Barium Sulfate in order to be radiopaque. Tip 192 includes guidewire lumen 191, a through hole which travels proximally, through control shaft 184, and exits handle 195 at guidewire exit hole 199, configured such that ablation device 180 can be percutaneously advanced over a guidewire which has had its distal end inserted into a pulmonary vein of the patient.

Handle 195, preferably made of a plastic such as a polycarbonate, includes lever 196 which is operably attached to one or more pull wires, not shown, that travel within a lumen of outer shaft 182 and attach near the distal end of shaft 182. Multiple pull wires may be included, such as two pull wires which are attached at a 90° radial separation from each other near the distal end of shaft 182. The two pull wires may be attached at the same longitudinal position along the axis of shaft 182, or may be offset. Manipulation of lever 196 causes the distal portion of ablation catheter 180 to deflect in one or more planes such that a clinician can manipulate tip 192 into a pulmonary vein or other orifice such as the coronary sinus or other vessel.

Handle 195 also includes plug 198 which is configured to electrically connect to one or more separate devices, such as an energy delivery unit configured to deliver ablation energy to electrodes 188 and/or to receive temperature signals from one or more temperature sensors such as a thermocouple integral to an electrode 188; a mapping unit configured to receive electrical signals from one or more electrodes 188; a pacing unit configured to deliver electrical energy to electrodes 188 in order to pace the heart of a patient; or another device such as a device which receives and/or transmits signals to one or more functional elements of carrier assembly 185. Wires, not shown, attach to plug 198 and travel through handle 195, through outer shaft 182 and attach to electrodes 188 and any other sensors or transducers integral to electrodes 188 or attached to carrier arm 186. The wires may be located on the external surface of carrier arm 186, or travel within a lumen of carrier arm 186, exiting through a side hole to attach to electrodes 188.

Referring additionally to FIG. 12*b*, carrier assembly 185 is shown in a linear configuration such that ablation device 180 can be intraluminally advanced through the vasculature of the patient. Carrier assembly 185 is placed in this linear configuration by advancing control shaft 184 such as via rotating knob 193 of handle 195. Referring now to FIG. 12*c*, control shaft 184 is being retracted, and carrier assembly 185 is transitioning to a partial circumferential (less than 360°) loop. Advancement and retraction of control shaft 184 adjust the geometry of the loop, wherein full advancement causes a near-linear configuration and retraction causes the diameter of carrier assembly 185 to increase. Preferred maximum diameters of carrier assembly 185 are typically 15-32 mm to accommodate the varied anatomical contours neighboring pulmonary vein ostia (including non-circular ostia). The simplified loop-modifying controls of the present invention allow for rapid positioning by an operator. In a preferred embodiment, carrier arm 186 is resiliently biased (such as with the heat treating of a Nitinol component) in a helical configuration. In an alternative embodiment, carrier arm 186 is resiliently biased in a near-linear configuration. In the configuration where carrier arm 186 includes a wire surrounded by a sleeve, a resilient bias can be provided by the wire or the sleeve.

In another alternative embodiment, the proximal end of carrier arm 186 exits outer shaft 182 at a location approximate 90° radially offset from the location that carrier arm 186 is attached to the distal end of control shaft 184, such offset attachment providing a bias for forming the loop during retraction of control shaft 184.

Carrier assembly 185 may include a loop of 360° or more. In another alternative embodiment, outer shaft 182 may include a mechanical key to maintain the rotational orientation of control shaft 184 and/or carrier arm 186. Control shaft 184 may include an attachment ring near its distal end such as for attachment to the proximal end of carrier arm 186. In another preferred embodiment, carrier assembly 185 includes at least one temperature sensor more distal than the most distal ablation element delivering ablation energy, such that the maximum distal (e.g. into the pulmonary vein lumen) temperature is always monitored (e.g. to prevent creation of a pulmonary vein stenosis). In the configuration of FIGS. 12*a* through 12*c*, both control shaft 184 and carrier arm 186 exit the distal end of outer shaft 182. In an alternative embodiment, either or both control shaft 184 or carrier arm 186 exit a side hole of outer shaft 182 (not shown but near the distal end of outer shaft 182). In another alternative embodiment, control shaft 184 may be rotated, such as via a control on handle 195, to further change the geometry of carrier assembly 185.

Figure 13:
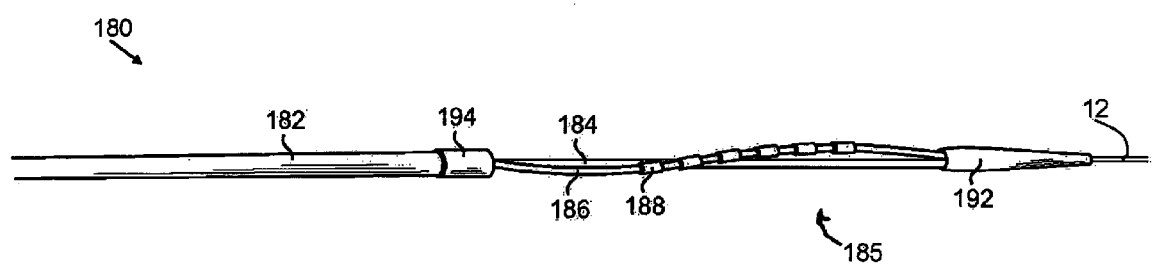
FIG. 13 illustrates a distal portion of an ablation catheter consistent with the present invention, in which the carrier assembly comprises a single carrier arm whose distal end is attached along a different axis than the proximal end.
Figure 13A:
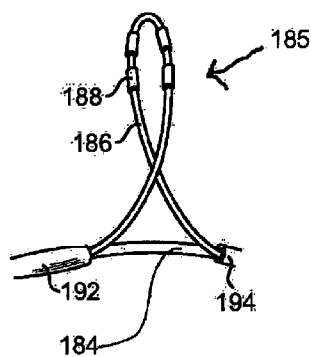
FIG. 13a illustrates a side view of a distal portion of the catheter of FIG. 13.
Figure 13B:
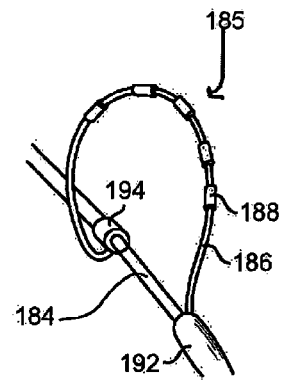
FIG. 13b illustrates a perspective view of a distal portion of the catheter of FIG. 13.

Referring now to FIGS. 13, 13*a* and 13*b*, the ablation catheter of FIG. 12*a* is illustrated. In FIG. 13, ablation catheter 180 is shown with carrier assembly 185 in linear configuration such as for advancing ablation catheter 180 over guidewire 12, such as an intraluminal advancement over a guidewire which has been inserted into a femoral vein, and travels to the heart, through the septum separating the right atrium and left atrium (e.g. through a transeptal sheath), and into a pulmonary vein such as the left superior pulmonary vein. Carrier assembly 185 is placed in this linear, maximally compact configuration by advancing control shaft 184, such as by manipulating a control on a handle of device 180 as has been described hereabove. Carrier arm 186 includes electrodes 188. Carrier arm 186 has a proximal end fixedly attached to outer shaft 182 via crimp ring 194. Carrier arm 186 distal end is fixedly attached to control shaft 184 at a radial location that is 90° offset from its proximal end attachment (as shown in FIG. 13), such that carrier assembly 185 radially expands as shown in FIGS. 13*a* and 13*b* as control shaft 184 is retracted. The distal end of control shaft 184 is covered with atraumatic tip 192, which includes an exit hole in communication with an internal guidewire lumen, not shown but through which guidewire 12 passes.

Referring now to FIG. 14, a preferred construction of the ablation catheter of FIG. 12*a* is illustrated. Ablation catheter 180 includes carrier assembly 185, which comprises a single carrier arm 186 whose geometry is adjusted by advancing and retracting control shaft 184, as has been described in detail hereabove. Carrier arm 186 includes wire shaft 202, preferably Nitinol or other shaped memory alloy or polymer, surrounded by outer sleeve 203, preferably Pebax or other biocompatible, soft material. Sleeve 203 can perform one or more functions, including but not limited to: capturing one or more wires between wire 202 and sleeve 203; acting as an insulator; providing an atraumatic boundary (e.g. covering any sharp edges of wire 202); and combinations thereof. Wire shaft 202 preferably is resiliently biased in the loop geometry depicted. The proximal end of carrier arm 186 is fixedly attached to outer shaft 182 via ring 194. Alternatively or additionally, adhesives such as cyanoacrylate may be used for fixation. In an alternative embodiment, ring 194 also functions as an electrode, such as a mapping and/or ablation electrode.

At its distal end, carrier arm 186 is fixedly attached to cap 192 and the distal end of control shaft 184. Cap 192 is of soft construction to be atraumatic to tissue, and is preferably made of Pebax which has been doped with Barium Sulfate to be radiopaque. A guidewire lumen 201 exits cap 192 after having passed within control shaft 184. Guidewire lumen 201 is surrounded by a braided tube preferably made of Nylon and braided with stainless steel wire. The guidewire lumen 201 travels proximally to an exit port on a handle, not shown but described in detail hereabove.

Electrodes 188 are fixedly mounted to carrier arm 186, such as with cyanoacrylate (or other adhesive) beads 204. Each electrode 188 preferably includes a thermocouple, not shown but preferably a copper-constantan wire junction welded to an internal surface of electrode 188. Each electrode, and any included thermocouple, is attached to one or more wires (attachment not shown), which are grouped with other wires to form wire bundle 210, which travels proximally and is attached to an electrical port on the proximal end of ablation catheter 180. Carrier arm 186 may include other sensors or transducers, some of which may also be attached to wires included in wire bundle 210, these sensors or transducers placed against tissue such as pulmonary vein ostial tissue to perform a diagnostic or therapeutic procedure in a patient.

FIG. 14 further illustrates a preferred construction of the distal portion of outer shaft 182. Immediately proximal to ring 194 is distal segment 205, preferably made of Pebax 5533 or 6333. Immediately proximal to distal segment 205 is hinge segment 206, and proximal to hinge segment 206 is wall 212. Hinge segment 206 is preferably made of a softer material than distal segment 205 and wall 212, such as Pebax 3533. Mounted within hinge segment 206 is second anchor ring 211, a metal (e.g. stainless steel) ring that is fixedly attached to two (2) pull wires 209. Pull wires 209 extend proximally and are attached to a knob, lever or other control integral to a handle, all not shown but operably configured to deflect the distal end of ablation catheter 180 in multiple planes. Wall 212 surrounds braid 207 and braid 207 surrounds liner 208. Braid 207, a standard catheter braid to provide column and torsion support, is preferably made of stainless steel such as 304 stainless steel. Liner 208 is preferably made of Teflon or another lubricious material that allows one or more shafts, such as control shaft 184 and pull wires 209, to be slidingly received within a lumen of shaft 182 without significant resistance.

Referring now to FIGS. 15*a* through 15*d*, the ablation catheter of FIG. 12*a* is illustrated. Ablation catheter 180 includes outer shaft 182, control shaft 184, ring 194, carrier assembly 185 and tip 192, all of which include similar components, materials, construction and function to the same or like parts used in reference to the ablation catheters described hereabove. FIG. 15*a* illustrates the proximal portion, including handle, preferably made of a plastic such as polycarbonate. Handle 195 includes lever 196 and slide 197, controls used by an operator to adjust the carrier assembly, deflect the distal portion of catheter 180 and/or perform other functions. Handle 195 is fixedly attached to shaft 182. Extending from handle 195 is pigtail plug 198, an electrical connector that attaches signal and power wires to one or more components of ablation catheter 180 such as ablation electrodes, mapping electrodes and thermocouples.

Referring now to FIG. 15b, the distal end of catheter 180 is illustrated including the distal end of outer shaft 182. FIG. 15b illustrates carrier assembly 185 in its compacted, linear configuration applicable for over-the-wire intraluminal advancement of ablation catheter 180, such as to reach the left superior pulmonary vein as depicted in FIG. 15d. Referring back to FIG. 15b, control shaft 184 has been fully advanced such that carrier arm 186 is pulled tight against control shaft 184. Control shaft 184 includes on its distal end tip 192. Within tip 192 is guidewire lumen 191 through which a standard interventional guidewire, such as a 0.035" guidewire, can be inserted. Carrier assembly 185 is configured, as has been described in detail hereabove, such that upon retraction of control shaft 184, carrier arm 186 extends laterally into the loop configuration illustrated in FIG. 15c.

Referring additionally to FIG. 15d, the treatment to be accomplished with the devices and method described in this application is illustrated. FIG. 15d shows a cutaway view of the human heart 10, showing the major structures of the heart including the left and right atria, and the pulmonary veins 15. The atrial septum separates the left and right atria. The fossa ovalis is a small depression in the atrial septum that may be used as an access pathway to the left atrium from the right atrium, such as with a transeptal puncture device and transeptal sheath. The fossa ovalis can be punctured, and easily reseals and heals after procedure completion. In a patient suffering from atrial fibrillation, aberrant electrically conducive tissue may be found in the atrial walls, as well as in the pulmonary veins 15. Ablation of these areas, referred to arrhythmogenic foci (also referred to as drivers or rotors), is an effective treatment for atrial fibrillation. The catheters of the present invention provide means of creating lesions, including lesions to surround the pulmonary vein ostia, and are easily deployed to identify and ablate the driver and rotor tissue.

To accomplish this, catheter 180 is inserted into the right atrium, preferably through the inferior vena cava, as shown in the illustration, or through the superior vena cava. Catheter 180 is sized for this advancement through the patient's vasculature, such as where the inserted (shaft) diameter is approximately 9 Fr, the shaft length is approximately 115 cm and the overall length is typically 158 cm. Catheter 180 has been passed through transeptal sheath 11, which may or may not be a deflectable sheath since catheter 180 preferably includes a deflectable distal portion. When passing into the left atrium, transeptal sheath 11 passes through or penetrates the fossa ovalis, such as over guidewire 12 which may have been placed by a transeptal puncture device. Catheter 180 is inserted over guidewire 12 and through transeptal sheath 11 such that its distal end enters right superior pulmonary vein 15's lumen. The distal portion of shaft 182 has been deflected such that the distal end of shaft 182 is directed toward the lumen of pulmonary vein 15a. Catheter 180 carries a structure carrying multiple ablation elements such as RF electrodes, carrier assembly 185, into the left atrium. Carrier assembly 185 has been transitioned to expand to a maximal diameter by retracting control shaft 184, such that multiple ablation elements (ablation and/or mapping elements), electrodes 188, are in contact with the pulmonary vein ostial tissue. Carrier assembly 185 is adapted to be deformable such that pressing carrier assembly into pulmonary vein 15 ostium will cause one or more, and preferably all of electrodes 188 to make contact with tissue to be analyzed and/or ablated. Each of the electrodes 188 is attached via connecting wires and one or more connectors, such as plug 198, to an energy delivery apparatus, not shown but preferably an RF energy delivery unit which is also attached to a patch electrode, also not shown but preferably a conductive pad attached to the back of the patient.

The energy delivery unit is configured to delivery RF energy in monopolar, bipolar or combination monopolar-bipolar energy delivery modes, simultaneously or sequentially, with or without "off" or no energy delivered time durations. In a preferred embodiment, the energy delivery unit 200 is configured to also provide electrical mapping of the tissue that is contacted by one or more electrodes integral to carrier assembly 185. Alternatively, a separate mapping unit may be used, preferably attached to catheter 180 simultaneous with attachment to the energy delivery unit. Electrodes 188 can also be configured to be mapping electrodes and/or additional electrodes can be integral to carrier assembly 185 to provide a mapping function. Carrier assembly 185 is configured to be engaged over a pulmonary vein ostium surface to map and/or ablate tissue on the surface. Energy is delivered after a proper location of the electrodes 188 is confirmed with a mapping procedure. If conditions are determined to be inadequate, an operator may adjust the shape of carrier assembly 185 (e.g. through advancement or retraction of control shaft 184) and/or the operator may reposition carrier assembly 185 against tissue through various manipulations at the proximal end of the ablation catheter 180. After an ablation step is completed, ablation catheter 180 is repositioned, with or without changing the geometry of carrier assembly 185, and a similar mapping and ablation step is performed. For each pulmonary vein ostium, this repositioning will typically occur two to three times creating semi-circular lesions that preferably overlap. The steerability of the distal portion of shaft 182, via a control on handle 195, is an important function in this repositioning process. In a typical procedure, the clinician will perform ablations in the left superior pulmonary vein first, followed by the right superior, left inferior and then the right inferior pulmonary veins.

In a preferred embodiment, the energy delivery unit is configured to delivery both RF energy and ultrasound energy to the identical or different electrodes 188. In another preferred embodiment, the energy delivery unit is configured to accept a signal from one or more sensors integral to ablation catheter 180, not shown, such that the energy delivered can be modified via an algorithm which processes the information received from the one or more sensors.

In an alternative embodiment, a guidewire is inserted through a sidecar present at the distal portion of shaft 182, avoiding the need for threading the entire the device over the guidewire. In another alternative embodiment, carrier arm 186 is attached to a second control shaft, also slidingly received by outer shaft 182 and connected to a control on handle 195, such that the carrier assembly 185 geometry can be adjusted by advancing and retracting either the second control shaft or control shaft 184. This dual control shaft design also allows carrier assembly to be completely retracted within the distal end of outer shaft 182, as is described in reference to FIG. 17 herebelow.

Figure 16:
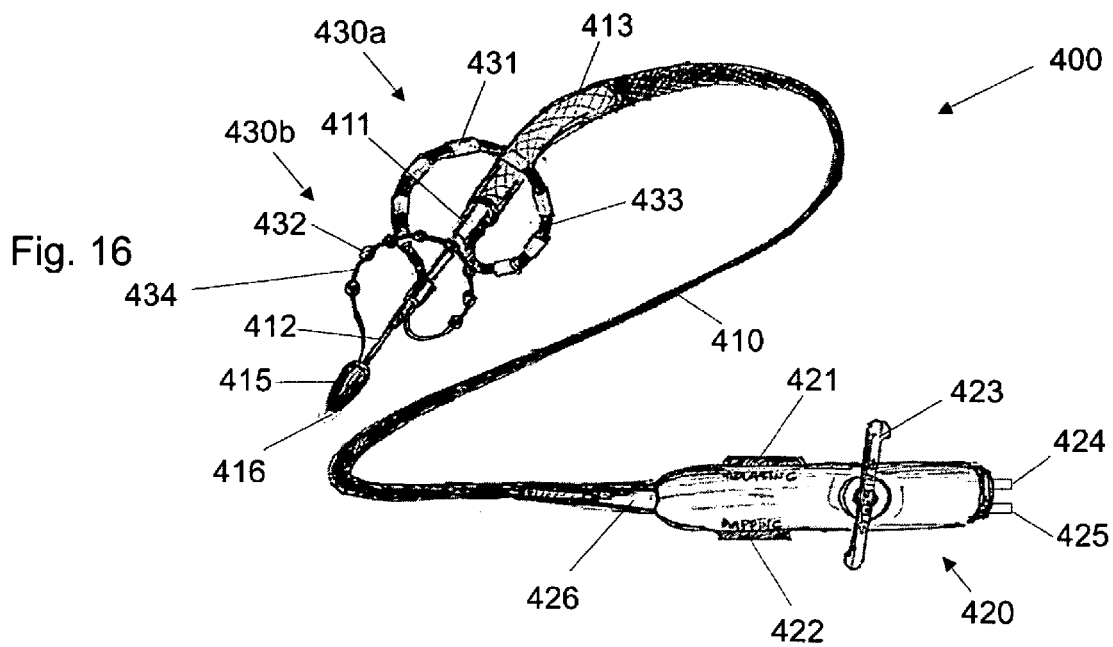
FIG. 16 illustrates a perspective view of an ablation catheter consistent with the present invention, including a first deployable carrier assembly and a second deployable carrier assembly.

Referring now to FIG. 16, an ablation catheter of the present invention is illustrated comprising a first deployable carrier assembly including multiple ablation electrodes and a more distal second deployable carrier assembly including multiple mapping electrodes. Ablation catheter 400 includes outer shaft 410, first control shaft 411, second control shaft 412, first carrier assembly 430a, second carrier assembly 430b and tip 415, all of which include similar components, materials, construction and function to the same or like parts used in reference to the ablation catheters described hereabove. Outer shaft 410, preferably a braided construction including braid 413, slidingly receives first control shaft 411, which in turn slidingly receives second control shaft 412. Outer shaft 410 is fixedly attached to handle 420 via strain relief 426. An atraumatic tip 415 is fixedly attached to the distal end of second control shaft 412. A guidewire lumen 416 exits tip 415 and travels proximally, through second control shaft 412, first control shaft 411 and outer shaft 410 to handle 420 where it exits via guidewire entry 424, such that ablation catheter 400 can be percutaneously introduced into a patient over a previously placed guidewire.

First carrier assembly 430a comprises a single carrier arm, first carrier arm 433, which is fixedly attached on its distal end to the distal end of first control shaft 411 and on its proximal end to the distal end of outer shaft 410. First control shaft 411 is operably connected on its proximal end to first advancable knob 421, such that advancement and retraction of knob 421 causes advancement and retraction of first control shaft 411. Advancement and retraction of first control shaft 411 causes first carrier assembly 430a to contract and expand, respectively, as has been described hereabove. Full advancement of first control shaft 411 causes first carrier assembly 430a to have a minimum diameter (fully constrained near-linear configuration) and full retraction of control shaft 411 causes first carrier assembly 430a to have a maximum diameter. First carrier assembly 430a includes electrodes 431, and each electrode 431 is preferably at least configured to deliver ablation energy to tissue.

Second carrier assembly 430b comprises a single carrier arm, second carrier arm 434, which is fixedly attached on its distal end to the distal end of second control shaft 412 and on its proximal end to the distal end of first control shaft 411. Second control shaft 412 is operably connected on its proximal end to second advancable knob 422, such that advancement and retraction of knob 422 causes advancement and retraction of second control shaft 412. Advancement and retraction of first control shaft 411 (via advancement and retraction of knob 421) causes second carrier assembly 430b to expand and contract, respectively. Also, advancement and retraction of second control shaft 412 (via advancement and retraction of knob 422) causes second carrier assembly 430b to contract and expand, respectively, as has been described hereabove. Advancement and retraction of first control shaft 411 and second control shaft 412, in combination or independently, changes the geometry of second carrier assembly 430b accordingly. For intraluminal advancement of ablation catheter 400, both first carrier assembly 430a and second carrier assembly 430b are placed in a minimal diameter configuration. Second carrier assembly 430b includes electrodes 432, and each electrode 432 is preferably at least configured to record electrical activity present in tissue. Electrodes 431 and electrodes 432 preferably include an integral temperature sensor, such as a thermocouple constructed of a copper-constantan bimetallic assembly. Electrodes 431 may be further configured to record electrical signals in tissue and electrodes 432 may be further configured to deliver ablation energy to tissue.

Handle 420 also includes lever 423, which is operably attached to one or more pull wires which extend distally within a lumen, such as a Teflon lined lumen, within outer shaft 410. The one or more pull wires are fixedly attached to a distal portion of outer shaft 410 causing operator controlled deflection of the distal portion of ablation catheter 400 in one or more planes. Handle 420 further includes electrical plug 425 which is electrically connected to one or more electrical wires or other conduits, all of which travel distally, along outer shaft 410 to various locations such as electrodes 431 or electrodes 432, or another sensor or transducer not shown. Plug 425 is configured to attach to an energy delivery unit such as an RF energy delivery unit, a mapping unit or another device configured to transmit or receive electrical signals or power.

Figure 16A:
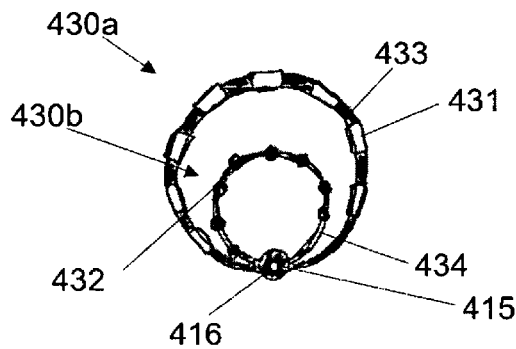
FIG. 16a illustrates an end view of the ablation catheter of FIG. 16.
Figure 16B:
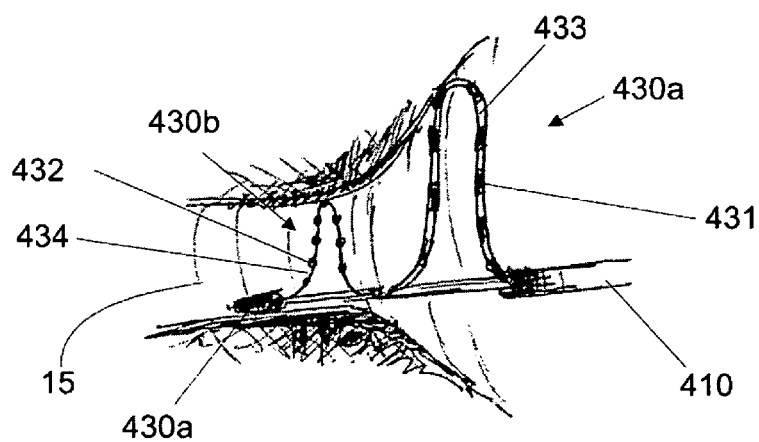
FIG. 16b illustrates a side sectional view of the distal portion of the ablation catheter of FIG. 16, wherein the distal carrier assembly is in contact with the lumen of a pulmonary vein and the proximal carrier assembly is in contact with the pulmonary vein ostium.

FIG. 16a illustrates an end view of the ablation catheter of FIG. 16. First carrier assembly 430a and second carrier assembly 430b are both in their maximum diameter configurations. FIG. 16b illustrates a side view of the ablation catheter of FIGS. 16 and 16a inserted into a vessel, such as a pulmonary vein 15, through its ostium. Second carrier assembly 430b is partially or fully expanded and in contact with the luminal wall of vein 15. First carrier assembly 430a is partially or fully expanded and engaging the ostium of vein 15.

Figure 17:
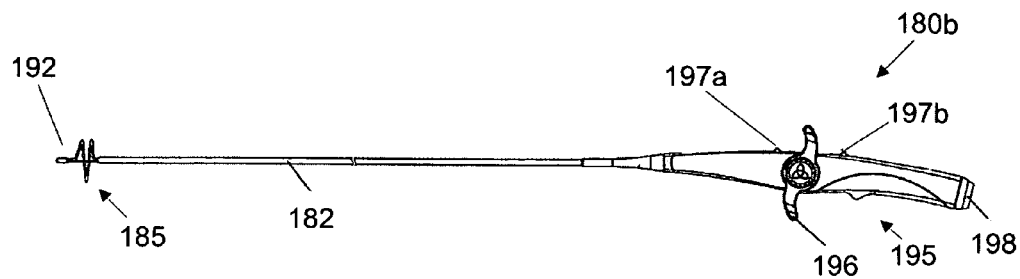
FIG. 17 illustrates a side view of an ablation catheter consistent with the present invention, including a carrier assembly comprising a single carrier arm that can be fully retracted within a lumen of the shaft of the device.

Referring now to FIGS. 17, 17a, 17b and 17c, an ablation catheter of the present invention is illustrated. Ablation catheter 180b is of similar construction to ablation catheter 180 of FIGS. 12 through 14 with common elements having the same reference numbers. For brevity, most of the common construction and common component details will be omitted. Ablation catheter 180b includes handle 195 with operator controls first slide 197a, second slide 197b and lever 196, each operably attached to a control shaft or other linkage. Plug 198 is connected to one or more electrical wires or other conduits that travel distally through outer shaft 182 and connect to one or more functional elements of the device, such as electrodes included in carrier assembly 185. The distal end of ablation catheter 192 includes an atraumatic tip 192, preferably constructed of Pebax which has been doped with Barium Sulfate for radiopacity. The ablation catheter 180b of FIG. 17 depicts the carrier assembly 185 in a fully deployed (maximum diameter) configuration, caused by retracting the control shaft via a slide or lever on handle 195.

Figure 17A:
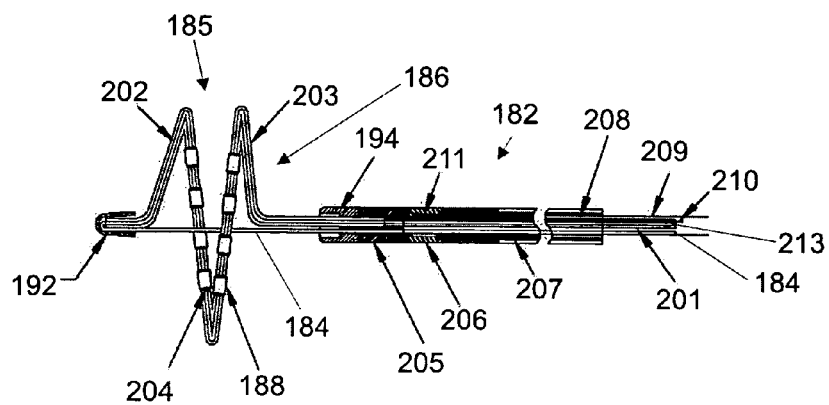
FIG. 17a illustrates a side sectional view of the device of FIG. 17 wherein the carrier assembly has been fully deployed.

Referring now to FIG. 17a, carrier arm carrier assembly 185 is in its fully deployed (maximum diameter) condition. Carrier arm 186 is attached on its distal end to the distal end of first control shaft 184. On its proximal end, instead of being attached to the distal portion of outer shaft 182 as the ablation device 180 of FIG. 12a, carrier arm 186 is attached to a second control shaft 213, which also can be advanced and retracted from a control on handle 195. Advancement and retraction of both first control shaft 184 and second control shaft 213 can be used, independently or in combination, to change the geometry of carrier assembly 185.

Figure 17B:
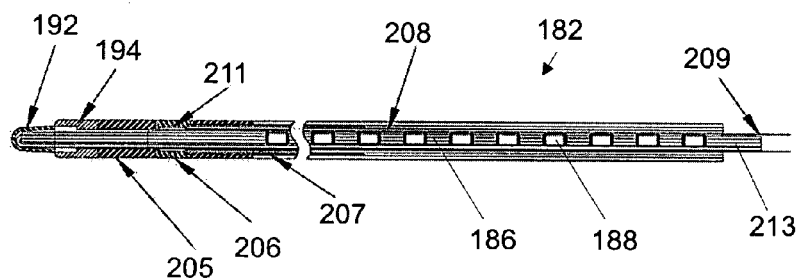
FIG. 17b illustrates a side sectional view of the device of FIG. 17 wherein the carrier assembly has been fully compacted.

Referring now to FIG. 17b, a differentiating feature of ablation catheter 180b is illustrated where second control shaft 213 has been retracted until carrier arm 186, including ablation elements 188, is contained completely within a lumen of outer shaft 182, such as within a lumen within a Teflon liner. In an alternative embodiment, carrier arm 186 is retracted within outer shaft 182 by retracted first control shaft 184.

Figure 17C:
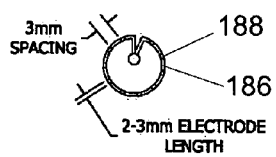

Referring now to FIG. 17c, an end view of the device and deployment status of FIG. 17a is illustrated. Carrier arm 186 is shown in its less than 360° helix. Also shown are electrodes 188, typically 2-3 mm in length with symmetric 3 mm spacing between electrodes.

It should be understood that numerous other configurations of the systems, devices and methods described herein can be employed without departing from the spirit or scope of this application. It should be understood that the system includes multiple functional components, such as the ablation catheter and the energy delivery apparatus. The ablation catheter consists of a catheter shaft, a carrier assembly for providing electrodes in a resiliently biased configuration, a control shaft for deploying and withdrawing the carrier assembly, and a coupler for attaching the control shaft to the carrier assembly.

The carrier assembly is a support structure which is shiftable from a storage or confined configuration, such as a radially constrained configuration, to a deployed or expanded configuration. The carrier assembly can includes wires, ribbons, cables and struts, made of either metals, non-metals or combinations of both. The carrier assembly can be constructed of one or more materials, including both metals and non-metals. Typical metals chosen for carrier assembly construction include but are not limited to: stainless steel, Nitinol, Elgiloy™, other alloys and combinations thereof.

The ablation catheter of the present invention may include a steerable outer sheath, or may work in conjunction as a system with a separate steerable outer sheath. One or more tubular components of the ablation catheter may be steerable such as with the inclusion of a controllable pull wire at or near the distal end. The ablation catheter of the present invention may be inserted over the wire, such as via a lumen within one of the tubular conduits such as within a lumen of the tubular body member or control shaft, or alternatively the catheter may include a rapid exchange sidecar at or near its distal end, consisting of a small projection with a guidewire lumen therethrough. A guidewire lumen may be included solely for the guidewire, or may provide other functions such as a vacuum lumen for an integral suction port integrated at the distal portion of the carrier assembly.

The ablation catheter of the present invention further includes ablation elements. In preferred embodiments, one or more ablation elements are electrodes configured to deliver RF energy. Other forms of energy, alternative or in addition to RF, may be delivered, including but not limited to: acoustic energy and ultrasound energy; electromagnetic energy such as electrical, magnetic, microwave and radiofrequency energies; thermal energy such as heat and cryogenic energies; chemical energy; light energy such as infrared and visible light energies; mechanical energy; radiation; and combinations thereof. One or more ablation elements may comprise a drug delivery pump or a device to cause mechanical tissue damage such as a forwardly advanceable spike or needle. The ablation elements can deliver energy individually, in combination with or in serial fashion with other ablation elements. The ablation elements can be electrically connected in parallel, in series, individually, or combinations thereof. The ablation catheter may include cooling means to prevent undesired tissue damage and/or blood clotting. The ablation elements may be constructed of various materials, such as plates of metal and coils of wire for RF energy delivery. The electrodes can take on various shapes including shapes used to focus energy such as a horn shape to focus sound energy, and shapes to assist in cooling such as a geometry providing large surface area. Electrodes can vary within a single carrier assembly, such as a spiral array of electrodes or a umbrella tip configuration wherein electrodes farthest from the central axis of the catheter have the largest major axis. Wires and other flexible conduits are attached to the ablation elements, such as electrical energy carrying wires for RF electrodes or ultrasound crystals, and tubes for cryogenic delivery.

The ablation elements requiring electrical energy to ablate require wired connections to an electrical energy power source such as an RF power source. In configurations with large numbers of electrodes, individual pairs of wires for each electrode may be bulky and compromise the cross-sectional profile of the ablation catheter. In an alternative embodiment, one or more electrodes, connected in serial fashion such that a reduced number of wires, such as two wires, can be attached to two or more electrodes, include switching means such that while a first electrode is powered, the remaining electrodes do not transmit ablative energy. Switching means may be a thermal switch, such that as a first electrodes heats up, a single pole double throw switch change state disconnecting power from that electrode and attaching power to the next electrode in the serial connection. This integral temperature switch may have a first temperature to disconnect the electrode, and a second temperature to reconnect the electrode wherein the second temperature is lower than the first temperature, such as a second temperature below body temperature. In an alternative embodiment, each electrode is constructed of materials in their conductive path such that as when the temperature increased and reached a predetermined threshold, the resistance abruptly decreased to near zero, such that power dissipation, or heat, generated by the electrode was also near zero, and more power could be delivered to the next electrode incorporating the above switching means.

The ablation catheter of the present invention preferably includes a handle activating or otherwise controlling one or more functions of the ablation catheter. The handle may include various knobs, such as rotating or sliding knobs which are operably connected to advanceable conduits, or are operably connected to gear trains or cams which are connected to advanceable conduits. These knobs, such as knobs use to deflect a distal portion of a conduit, or to advance or retract the carrier assembly, preferably include a reversible locking mechanism such that a particular tip deflection or deployment amount can be maintained through various manipulations of the system.

The ablation catheter may include one or more sensors, such as sensors used to detect chemical activity; light; electrical activity; pH; temperature; pressure; fluid flow or another physiologic parameter. These sensors can be used to map electrical activity, measure temperature, or gather other information that may be used to modify the ablation procedure. In a preferred embodiment, one or more sensors, such as a mapping electrode, can also be used to ablate tissue.

Numerous components internal to the patient, such as the carrier assembly or electrodes, may include one or more visual markers such as radiopaque markers visible under fluoroscopy, or ultrasound markers.

Selection of the tissue to be ablated may be based on a diagnosis of aberrant conduit or conduits, or based on anatomical location. RF energy may be delivered first, followed by another energy type in the same location, such as when a single electrode can deliver more than one type of energy, such as RF and ultrasound energy. Alternatively or additionally, a first procedure may be performed utilizing one type of energy, followed by a second procedure utilizing a different form of energy. The second procedure may be performed shortly after the first procedure, such as within four hours, or at a later date such as greater than twenty-four hours after the first procedure. Numerous types of tissue can be ablated utilizing the devices, systems and methods of the present invention. For example, the various aspects of the invention have application in procedures for ablating tissue in the prostrate, brain, gall bladder, uterus, other organs and regions of the body, and a tumor, preferably regions with an accessible wall or flat tissue surface. In the preferred embodiment, heart tissue is ablated, such as left atrial tissue.

In another preferred embodiment of the system of the present invention, an ablation catheter and a heat sensing technology are included. The heat sensing technology, includes sensor means that may be placed on the chest of the patient, the esophagus or another area in close enough proximity to the tissue being ablated to directly measure temperature effects of the ablation, such as via a temperature sensor, or indirectly such as through the use of an infrared camera. In the described system, when a temperature or a surrogate temperature reaches a threshold, such as an adjustable threshold, the ablation energy is reduced or stopped, to one or more ablation elements. The threshold will depend on the location of the sensor means, as well as where the ablation energy is being delivered. The threshold may be adjustable, and may be automatically configured.

Numerous kit configurations are also to be considered within the scope of this application. An ablation catheter is provided with multiple carrier assemblies. These carrier assemblies can be removed for the tubular body member of the catheter, or may include multiple tubular body members in the kit. The multiple carrier assemblies can have different patterns, different types or amounts of electrodes, and have numerous other configurations including compatibility with different forms of energy.

Though the ablation device has been described in terms of its preferred endocardial and transcutaneous method of use, the array may be used on the heart during open heart surgery, open chest surgery, or minimally invasive thoracic surgery. Thus, during open chest surgery, a short catheter or cannula carrying the carrier assembly and its electrodes may be inserted into the heart, such as through the left atrial appendage or an incision in the atrium wall, to apply the electrodes to the tissue to be ablated. Also, the carrier assembly and its electrodes may be applied to the epicardial surface of the atrium or other areas of the heart to detect and/or ablate arrhythmogenic foci from outside the heart.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims. In addition, where this application has listed the steps of a method or procedure in a specific order, it may be possible, or even expedient in certain circumstances, to change the order in which some steps are performed, and it is intended that the particular steps of the method or procedure claim set forth herebelow not be construed as being order-specific unless such order specificity is expressly stated in the claim.

We claim:

1. An ablation catheter for performing a medical procedure on a patient comprising:
   an elongated, flexible, tubular body member having a proximal end, a distal end and a lumen extending therebetween;
   a first control shaft coaxially disposed and slidingly received within the lumen of the tubular body member; and
   a flexible carrier assembly retractable within the tubular body member including at least two discrete ablation elements configured to deliver energy to tissue;
   wherein retraction of the first control shaft causes the at least two discrete ablation elements to transform from a near linear geometry to a partial helical geometry; and
   a second control shaft slidingly received within the tubular body member, wherein a proximal end of the carrier assembly is attached to the second control shaft, and a distal end of the carrier assembly is attached to the first control shaft.

2. The catheter of claim 1 wherein the catheter is configured to create a continuous, curvilinear lesion in tissue of a patient.

3. The catheter of claim 2 wherein the catheter is configured to create lesions proximate the ostium of the pulmonary veins of a patient.

4. The catheter of claim 1 wherein the catheter is configured to treat a patient with an arrhythmia.

5. The catheter of claim 4 wherein the arrhythmia is atrial fibrillation.

6. The catheter of claim 1 wherein the catheter is configured to be advanced over a guidewire, wherein the distal end of the guidewire is placed in the pulmonary vein of the patient.

7. The catheter of claim 1 wherein the control shaft includes a proximal end and a distal end and a lumen extending therebetween, said lumen configured to slidingly receive a guidewire.

8. The catheter of claim 7 wherein at least one of the shaft proximal end, shaft distal end and shaft lumen includes a braided reinforcement.

9. The catheter of claim 8 wherein the braided reinforcement terminates proximally of the at least one of the shaft proximal end, shaft distal end and the shaft lumen.

10. The catheter of claim 1 wherein the first control shaft includes a distal end and an atraumatic cap at least partially surrounding said distal end.

11. The catheter of claim 10 wherein the carrier assembly includes a distal end and the atraumatic cap further surrounds at least a portion of said distal end of the carrier assembly.

12. The catheter of claim 11 wherein the atraumatic cap prevents motion between the distal end of the first control shaft and the distal end of the carrier assembly.

13. The catheter of claim 1 wherein the carrier assembly is resiliently biased in the near linear geometry.

14. The catheter of claim 1 wherein the carrier assembly is resiliently biased in the partial helical geometry.

15. The catheter of claim 1 wherein the carrier assembly comprises a single carrier arm including a proximal end and a distal end.

16. The catheter of claim 15 wherein the carrier arm proximal end is attached to the second control shaft, and the carrier arm distal end is attached to the first control shaft.

17. The catheter of claim 15 wherein the carrier arm includes a cross-sectional geometry selected from the group consisting of: circular; oval; triangular; rectangular; trapezoidal; and combinations thereof.

18. The catheter of claim 15 wherein the carrier arm is attached to the tubular body member at a location 90° offset from the attachment to the control shaft.

19. The catheter of claim 15 wherein the carrier arm exits the distal end of the tubular body member.

20. The catheter of claim 15 wherein the tubular body member includes a side hole proximal to its distal end, and the carrier arm exits said side-hole.

21. The catheter of claim 1 wherein the carrier assembly is made at least partially from Nitinol.

22. The catheter of claim 21 wherein the Nitinol is resiliently biased via a heat treatment.

23. The catheter of claim 1 wherein the carrier arm further comprises an interior volume and an outer surface, and wherein the carrier arm further includes at least one side hole configured to allow a wore to pass from a location inside the carrier arm to an electrode on the outer surface of the carrier arm.

24. The catheter of claim 1 further comprising at least one temperature sensor.

25. The catheter of claim 24 wherein the at least one temperature sensor is integral to an ablation element.

26. The catheter of claim 25, wherein the temperature sensor is located on the tissue to ablation element interface.

27. The catheter of claim 24 wherein the at least one temperature sensor is located at a point on the catheter more distal than the most distal ablation element.

28. The catheter of claim 1 wherein the carrier assembly is configured such that the ablation elements make contact with pulmonary vein ostium/antrum tissue of the patient when said ablation elements are in the partial helical geometry.

29. The catheter of claim 1 wherein the carrier assembly is configured such that refraction of the control shaft a first distance causes the ablation elements to make contact with pulmonary vein ostium tissue of the patient and retraction of the control shaft a second distance also causes the ablation elements to make contact with pulmonary vein ostium tissue of the patient.

30. The catheter of claim 1 wherein at least one ablation element is an electrode configured to deliver at least electrical energy.

31. The catheter of claim 30, wherein the ablation element is radiopaque.

32. The catheter of claim 30, wherein the ablation element has a low thermal time constant.

33. The catheter of claim 1 wherein at least one ablation element is configured to deliver energy selected from the group consisting of: sound energy such as acoustic energy and ultrasound energy; electromagnetic energy such as electrical, magnetic, microwave and radiofrequency energies; thermal energy such as heat and cryogenic energies; chemical energy such as energy generated by delivery of a drug; light energy such as infrared and visible light energies; mechanical and physical energy; radiation; and combinations thereof.

34. The catheter of claim 1 wherein the at least two ablation elements are configured to deliver radiofrequency energy.

35. The catheter of claim 34 wherein at least one ablation element is configured to deliver monopolar energy to a ground pad.

36. The catheter of claim 34 wherein the at least two ablation elements are configured to transmit bipolar energy between said at least two ablation elements.

37. The catheter of claim 1 comprising at least four ablation elements.

38. The catheter of claim 37 comprising at least six ablation elements.

39. The catheter of claim 37 comprising at least eight ablation elements.

40. The catheter of claim 37 comprising at least ten ablation elements.

41. The catheter of claim 37 wherein said at least four ablation elements are substantially equally distributed along a line when the catheter is in a near linear configuration.

42. The catheter of claim 1 wherein the at least two discrete ablation elements are spaced apart at a distance between 1 and 4 mm.

43. The catheter of claim 1 wherein the at least two discrete ablation elements are spaced apart at a distance of about 1 mm.

44. The catheter of claim 1 wherein the at least two discrete ablation elements each have a length of about 3 mm.

45. The catheter of claim 1 wherein the at least two discrete ablation elements are further configured to map electrical signals present in tissue of a patient.

46. The catheter of claim 1 wherein the at least two discrete ablation elements are further configured to pace the heart of a patient.

47. The catheter of claim 1 wherein the at least two discrete ablation elements each include a heat-sinking fin.

48. The catheter of claim 1 wherein the carrier assembly has a helical diameter between 15 and 32 mm when said ablation elements are in the partial helical geometry.

49. The catheter of claim 1 further comprising a guidewire.

50. The catheter of claim 49 wherein the tubular body member is configured to slidingly receive the guidewire.

51. The catheter of claim 49 wherein the first control shaft is configured to slidingly receive the guidewire.

52. The catheter of claim 51 wherein the control shaft is configured to be advanceable toward a pulmonary vein ostium of a patient's heart after a distal end of the guidewire is placed into the pulmonary vein.

53. The catheter of claim 50 wherein the tubular body member includes a second lumen extending between its proximal and distal ends, and said second lumen slidingly receives the guidewire.

54. The catheter of claim 50 wherein the guidewire is fixedly attached to one of the tubular body member, control shaft, and carrier assembly.

55. The catheter of claim 1 further comprising a handle on the proximal end of the tubular body member.

56. The catheter of claim 55 wherein the handle includes a control configured to operably retract the first control shaft.

57. The catheter of claim 56 wherein the control is a rotating knob.

58. The catheter of claim 57 wherein the handle includes a control configured to manipulate delivery of energy to the tissue of a patient.

59. The catheter of claim 55 further comprising a pull wire and wherein the handle includes a control operably attached to said pull wire such that operation of the control deflects the distal end of the tubular body member in a first plane.

60. The catheter of claim 59 further comprising a second pull wire and wherein the handle includes a second control operably attached to said second pull wire such that operation of the second control deflects the distal end of the tubular body member in a second plane.

61. The catheter of claim 55 wherein the handle includes a control configured to rotate the first control shaft.

62. The catheter of claim 1 further comprising an anchoring element carried by the catheter configured to be anchored in a pulmonary vein of the patient.

63. The catheter of claim 62 wherein the anchoring element comprises a balloon.

64. The catheter of claim 62 wherein the anchoring element comprises an expandable cage.

65. The catheter of claim 62 wherein the control shaft includes a distal end and the anchoring element is configured to center said distal end in the pulmonary vein ostium.

66. The catheter of claim 1 wherein advancing the second control shaft causes the at least two discrete ablation elements to transform from a near linear geometry to a partial helical geometry.

67. An ablation catheter comprising:
an elongated, flexible, tubular body member having a proximal end, a distal end and a lumen extending therebetween;
a first control shaft coaxially disposed and slidingly received within the lumen of the tubular body member; and a flexible carrier assembly retractable within the tubular body member including at least two discrete ablation elements configured to deliver energy to tissue, wherein the carrier assembly comprises a single carrier arm including a proximal end and a distal end, wherein retraction of the first control shaft causes the at least two discrete ablation elements to transform from a near linear geometry to a partial helical geometry, and wherein the carrier arm is configured such that the same can be fully retracted within the tubular body member; and a second control shaft slidingly received within the tubular body member, wherein the proximal end of the carrier arm is attached to the second control shaft and the distal end of the carrier arm is attached to the first control shaft.

* * * * *